United States Patent
Lareau et al.

(10) Patent No.: US 11,538,558 B2
(45) Date of Patent: Dec. 27, 2022

(54) OPTIMIZATION OF GENE SEQUENCES FOR PROTEIN EXPRESSION

(71) Applicant: The Regents of the University of California, Oakland, CA (US)

(72) Inventors: Liana Faye Lareau, Berkeley, CA (US); Robert Tunney, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 519 days.

(21) Appl. No.: 16/597,856

(22) Filed: Oct. 10, 2019

(65) Prior Publication Data

US 2020/0294627 A1    Sep. 17, 2020

Related U.S. Application Data

(60) Provisional application No. 62/744,620, filed on Oct. 11, 2018.

(51) Int. Cl.
| | |
|---|---|
| *G16B 40/00* | (2019.01) |
| *G16B 5/00* | (2019.01) |
| *G16B 35/10* | (2019.01) |
| *G16B 30/00* | (2019.01) |
| *G01N 33/68* | (2006.01) |

(52) U.S. Cl.
CPC ......... *G16B 40/00* (2019.02); *G01N 33/6803* (2013.01); *G16B 5/00* (2019.02); *G16B 30/00* (2019.02); *G16B 35/10* (2019.02)

(58) Field of Classification Search
CPC ..... G01N 33/6803; G16B 40/00; G16B 30/00
See application file for complete search history.

(56) References Cited

U.S. PATENT DOCUMENTS

2013/0149699 A1* 6/2013 Barral ..................... C12P 21/02
435/68.1

OTHER PUBLICATIONS

Tunney et al, Accurate design of translational output by a neural network model of ribosome distribution, Jul. 2018, Nature Structural & Molecular Biology, vol. 25, pp. 577-587 (Year: 2018).*

* cited by examiner

*Primary Examiner* — Mark Halvorson
*Assistant Examiner* — Dennis J Sullivan
(74) *Attorney, Agent, or Firm* — Richard Aron Osman

(57) ABSTRACT

Gene sequences are tailored for protein expression by measuring ribosome dynamics, training a statistical model of the relationship between DNA sequence and translation speed; and using this model to design an optimal DNA sequence encoding a given protein.

10 Claims, 11 Drawing Sheets

Specification includes a Sequence Listing.

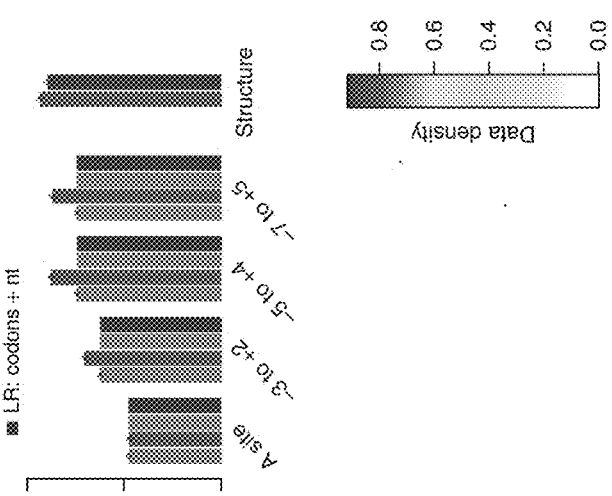
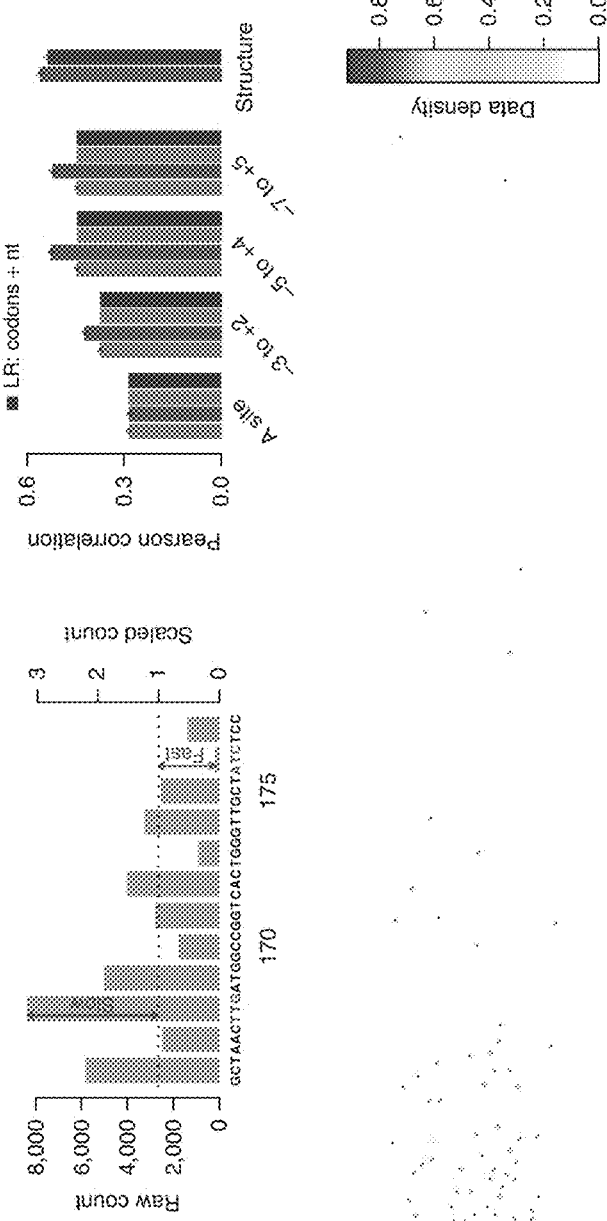
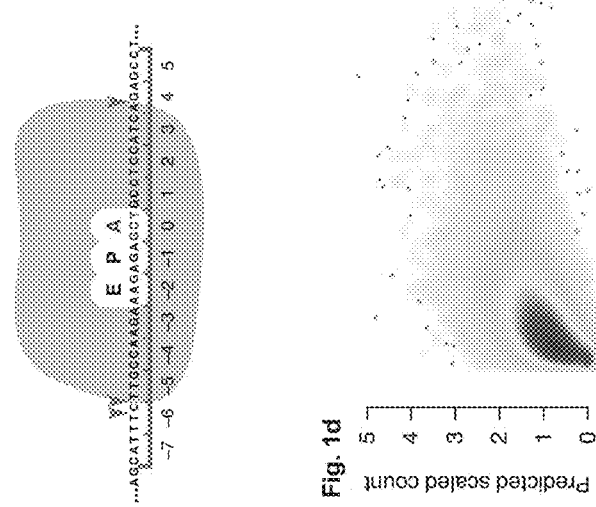
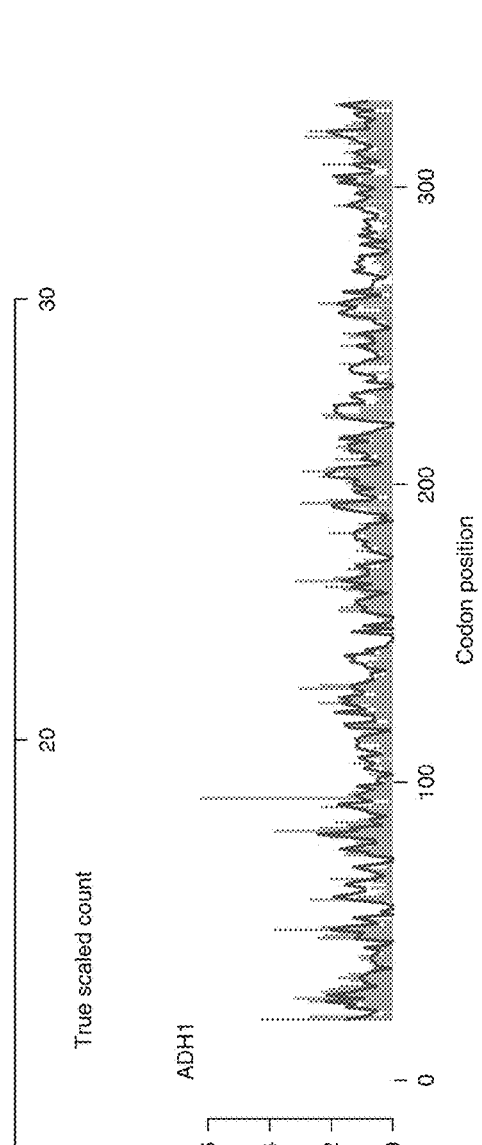
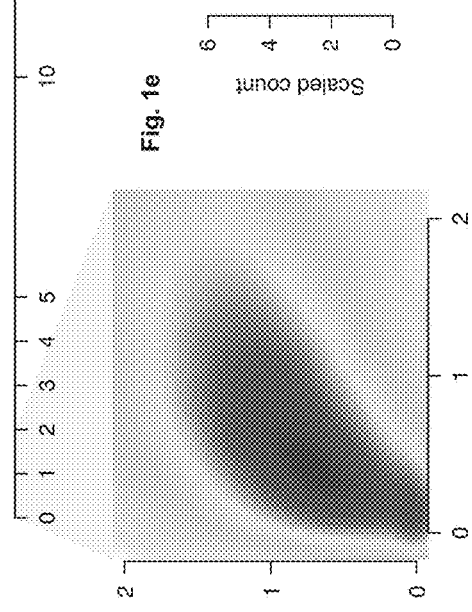

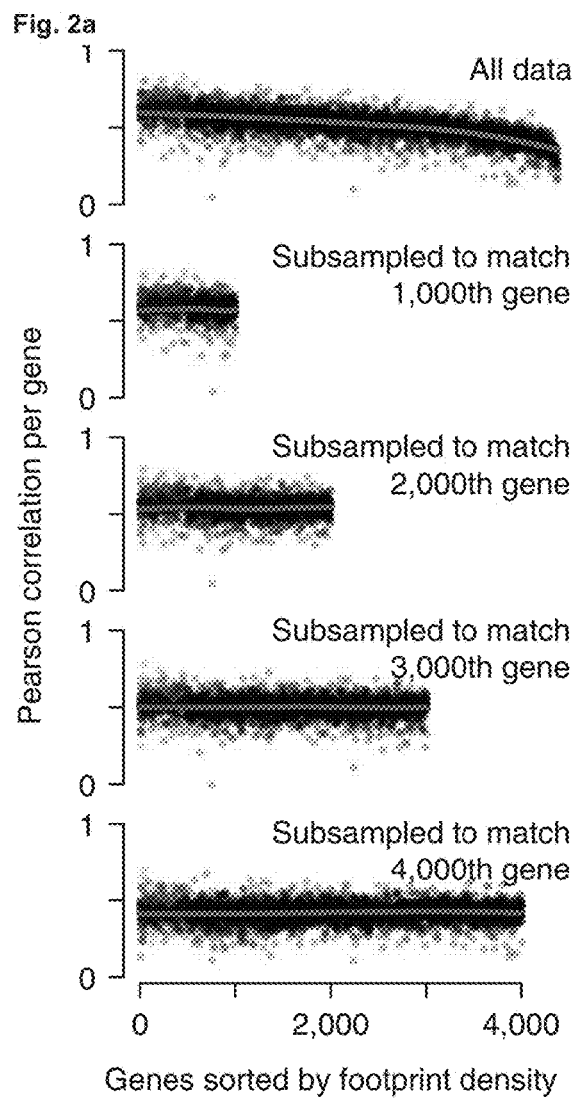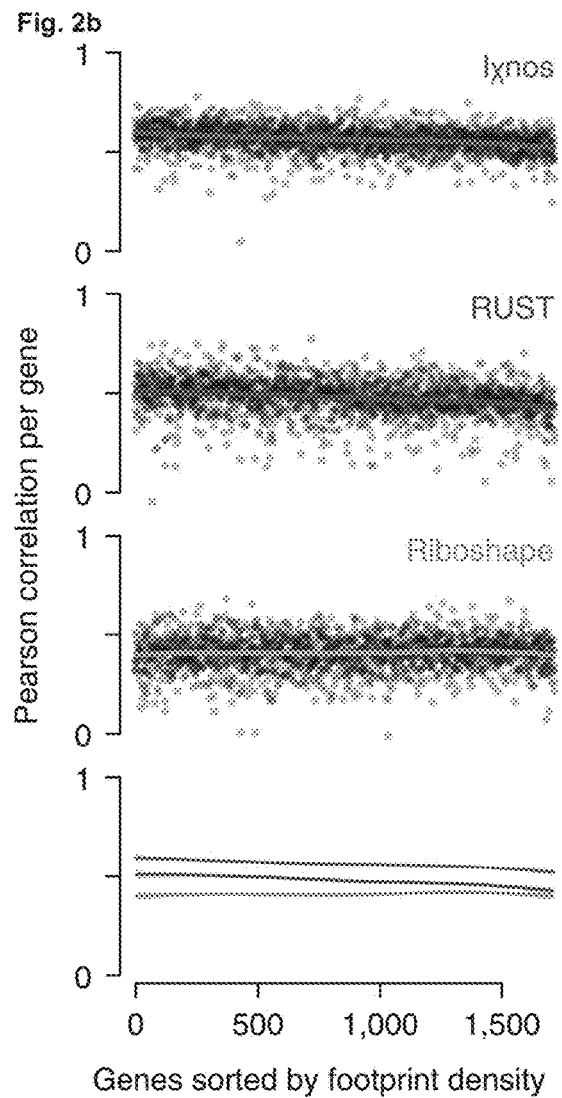

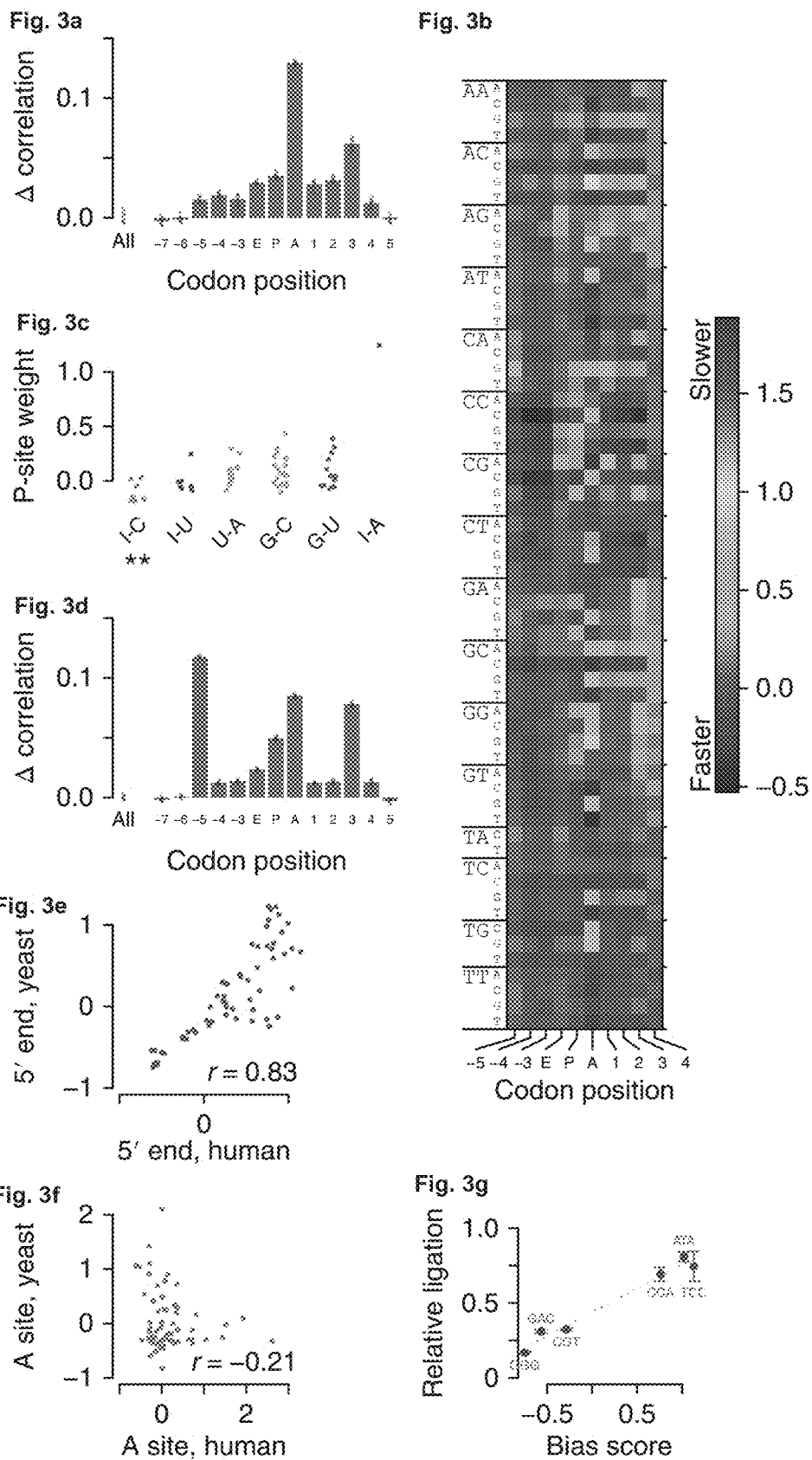

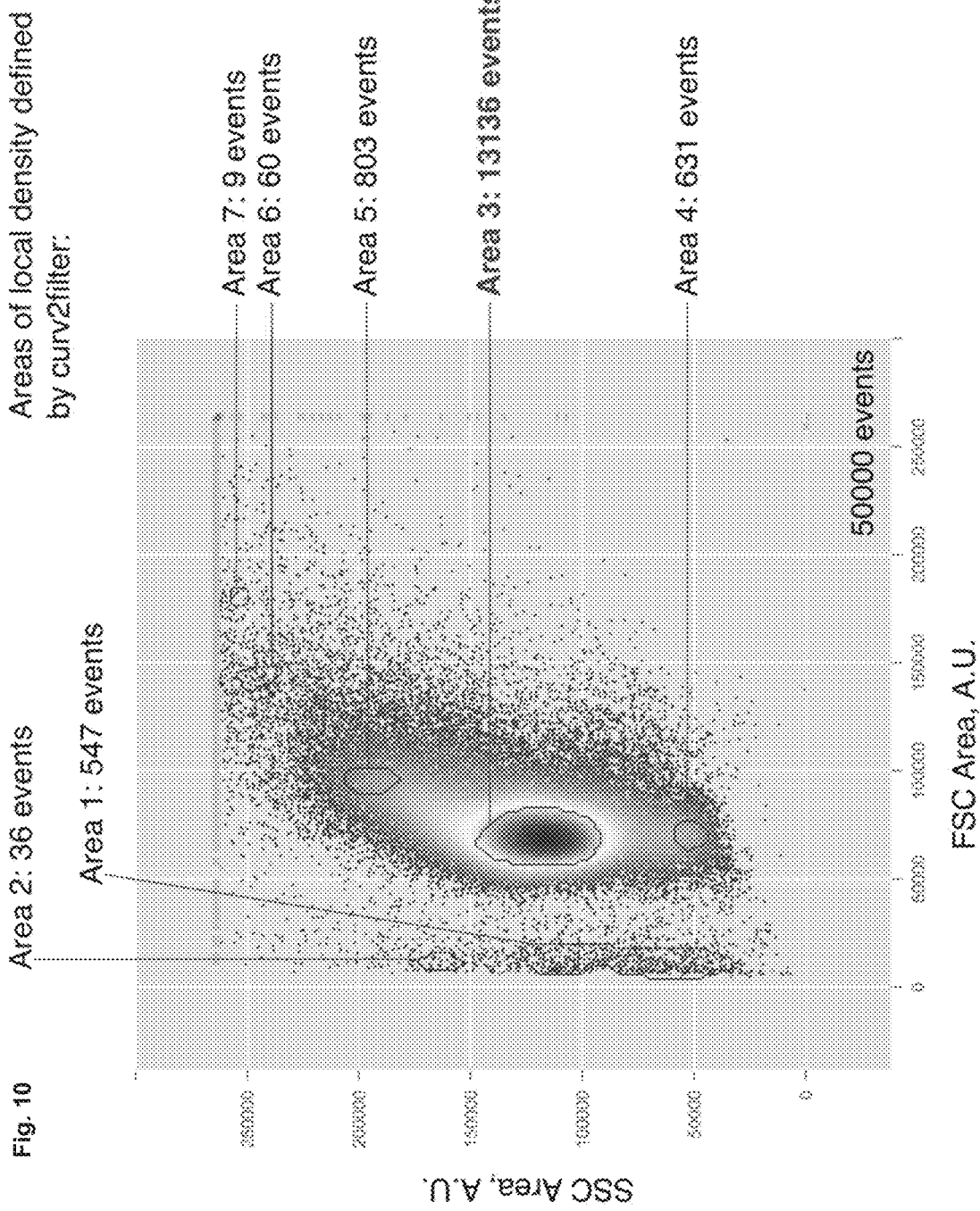

OPTIMIZATION OF GENE SEQUENCES FOR PROTEIN EXPRESSION

This invention was made with government support under Grant Numbers CA202960 and GM 102706 awarded by the National Institutes of Health. The government has certain rights in the invention.

This application incorporates by reference the material in the ASCII text file named "finalfiles_ST25", created Oct. 27, 2019, of size 7,915 bytes.

INTRODUCTION

Expression of a protein from one system (e.g., organism) in a different system is crucial in applications ranging from drug production to genetically modified food. We have developed a novel method to design genes that are optimized for protein expression in a given system.

A gene's DNA sequence encodes a protein, and these proteins are produced, or expressed, to carry out the functions of the cell. Bioengineering can take advantage of the cell as a protein production factory in order to produce heterologous proteins not originally encoded by that cell's genome. As examples, the high demand for insulin for diabetic patients is met by transferring the human insulin gene to bacteria that can then produce insulin in bulk, and genetically modified Bt corn expresses a protein from a bacterium that confers insect resistance. However, a gene from one organism is not always expressed properly in another organism.

Each amino acid in a protein can be encoded by any of up to six different codons, or three nucleotide DNA sequences, and different organisms favor different codons to encode the same protein. Use of non-preferred codons can slow down the ribosome, the cellular machine that produces protein, and prevent the cell from making protein. Thus, a 'foreign' gene sequence must often be modified to use the recipient host's preferred codons.

The challenge, then, is to identify the codon preferences of an organism and to re-encode the protein of interest using a preferred DNA sequence. To date, the methods to solve this problem have relied on indirect measurements of codon preference, such as frequency of a given codon in the host organism's genome.

Here, we take advantage of a method for measuring translation directly, combined with machine learning analysis, to learn the preferred codon sequences in an organism of interest. We use these results to design and demonstrate an optimized sequence encoding a protein of interest.

SUMMARY OF THE INVENTION

There is a large and growing market for better expression of heterologous genes in commercial and medical applications. Our method is an improvement over existing methods, and provides tailoring or optimizing gene sequences for protein expression, with myriad applications, such as:
- bulk production of proteins in microbial culture, such as bacteria or yeast production of biologics drugs in microbes or human cell culture
- expression of 'foreign' genes in plants or animals for genetically modified food production
- expression of enzymes in plants or microbes for synthetic biology production of compounds including biofuels
- expression of molecular biology markers such as green fluorescent protein in research organisms.

The invention provides for design of genes for expression in different human tissues for therapeutic use, and for design of sequences for any intermediate level of expression (not just highest or lowest) by generating random sequences and choosing one with an appropriate score. Hence, the methods are not limited to designing optimal sequences, but can fine-tune the output.

In an aspect the invention provides a method for tailoring or optimizing gene sequences for protein expression, comprising steps: (a) measure ribosome dynamics in the system of interest (ribosome profiling); (b) train a statistical model of the relationship between DNA sequence and translation speed; and (c) use this model to design an optimal DNA sequence encoding a given protein In an aspect the invention provides a method for tailoring gene sequences for protein expression, comprising steps: (a) measuring ribosome dynamics in an organism or cell type of interest to obtain ribosome profiling data; (b) training a statistical model of the relationship between DNA sequence and translation speed on the ribosome profiling data; and (c) using the trained model to design a DNA sequence encoding and tailored for expression of a protein of interest.

In embodiments:

step (a) comprises detecting RNA molecules bound ribosomes by ribosome profiling, which is deep sequencing of ribosome-protected mRNA fragments, and comprises contacting the RNA molecules with an enzymatic degradant or a chemical degradant thereby forming RNA fragments, wherein each RNA fragment comprises an RNA portion protected from the enzymatic degradant or the chemical degradant by a ribosome to which the RNA portion is bound; amplifying the RNA fragments to form amplified nucleic acid fragments; and detecting the amplified nucleic acid fragments, thereby detecting the RNA molecules bound to the ribosome;

the profiling data references ribosome E-P-A sites: aminoacyl site (A), the peptidyl site (P) and the exit site (E), and wherein step (b) comprises training the model to learn sequence preferences for translation by using counts of fragments at each position to learn the cell type or organism's sequence preferences for fast translation, by:

counting how many ribosomes are seen at each codon position in each gene, normalized by the average number of ribosomes per position in that gene;

using a machine learning protocol to learn a model for the position→normalized count relationship of the genome, wherein a 30-40 nucleotide window is encoded around each codon as a binary feature vector, and training a neural network and/or least squares (OLS) model to predict normalized counts as a function of these features, providing a model that can take as input any arbitrary gene sequence and predict how ribosomes will slow down or speed up on that sequence;

step (b) comprises:

predicting counts at the A site codon, wherein a sequence neighborhood spanning from 5 codons upstream of the A site (codon −5) to 4 codons downstream of the A site (codon +4) is used as the predictive region;

dividing the neighborhood into codons and encoded via one-hot encoding for input into a regression model, and encoding the same neighborhood as nucleotide features included in the model;

computing RNA structure score on three 30 nt sliding structure windows that span the width of a typical 28 nt footprint, wherein the windows start 17, 16, and 15 nucleotides before the start of the A site; and concatenating the features in a vector, and using the vector as the input to a fully connected feed-forward neural network model; and/or step (c) comprises using the model to design an optimized codon sequence to encode a given protein sequence by using a dynamic programming algorithm to determine an optimal codon sequence in the set of synonymous sequences that code for the protein.

In embodiments the methods further comprise synthesizing a DNA molecule of the DNA sequence.

The invention encompasses all combination of the particular embodiments recited herein, as if each combination had been laboriously recited.

BRIEF DESCRIPTION OF THE DRAWINGS

FIGS. 1A-E. Design and performance of a neural network model of translation elongation. a, Each ribosome protects an mRNA footprint of approximately 28-29 nt. Sequence coordinates in a neighborhood around a ribosome are indexed relative to the codon in the A site of the ribosome. b, Read count rescaling. For each gene, the counts of footprints assigned to each A site codon are divided by the average counts per codon over that gene. The resulting scaled footprint counts are used for model training and prediction. c, Model performances (Pearson correlations between predicted and true scaled counts over the test set) for neural network and linear regression models over a range of sequence neighborhoods, with and without nucleotide features, as well as correlations for models that also incorporate structure scores of the three 30-nt windows overlapping the footprint region, or the maximum structure score within 59 nt downstream of the ribosome. Bars show the mean of 10 runs of each model; the 10 individual runs for each model are overlaid as gray points. d, True vs. predicted scaled counts for the test set, under a model with codon and nucleotide features spanning codon positions −5 to +4. Color scale shows density of data points. e, True scaled counts (gray bars) and predicted scaled counts (red line) for a highly translated gene. Depicted sequences:

Figure 4A:
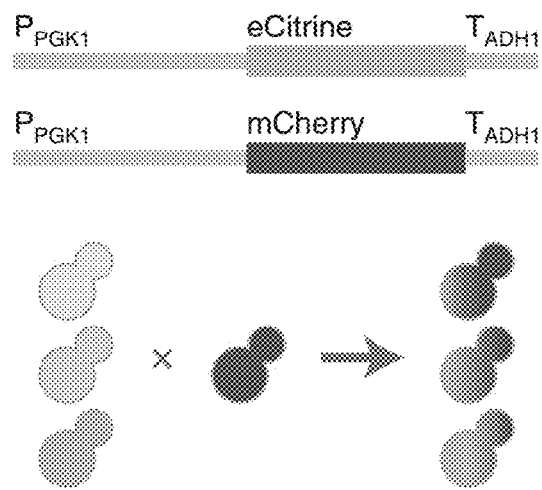

```
                                        (SEQ ID NO. 1)
AGCATTTCTTGCCAAGAAAGAGAGCTGCCTCCATCAGAGCCT
and
                                        (SEQ ID NO. 2)
GCTAACTTGATGGCCGGTCACTGGGTTGCTATCTCC.
```

FIGS. 2A-B. Performance comparisons on low coverage genes and with competing models. a, Top, per-gene correlations between true and predicted scaled counts, for all 4375 genes in our transcriptome that passed filtering criteria. Training set genes in blue (333/top 500 genes by footprint density). Loess curve on test set genes shown in red. Below, as above, with footprint counts on the top 1000, 2000, 3000, and 4000 genes subsampled to the density of footprint counts on the 1000th, 2000th, 3000th, and 4000th gene, respectively, and 'true' scaled counts recomputed. b, Comparison of Iχnos with similar models, RUST[19] and riboshape[15]. Shown are per-gene correlations between true and predicted scaled counts, on 1711 genes passing the filtering criteria from all three methods. Training set genes from Iχnos are excluded. Colored lines are loess curves, which are also compared in the bottom panel.

FIGS. 3A-G. Interpretation of models of translation elongation rates. a, Predictive value of codon positions in a yeast ribosome profiling dataset[22]. We computed Pearson correlations between true and predicted scaled counts on the test set, for a reference model including codon and nucleotide features from codon positions −7 to +5, and for a series of leave-one-out models, each excluding one codon position. Gray points show differences between Pearson's r for 10 runs of each leave-one-out model and the mean r of 10 runs of the reference model. Bars represent the mean of these values. b, Mean contributions to scaled counts by codon identity and position. c, P site codon contributions grouped by the codon:anticodon base pair formed by the third nucleotide of each codon. Asterisks indicate p<0.05 after Bonferroni correction, unpaired two-sided Mann-Whitney U test between each group and all other codons. I:C, p=0.014. d, Predictive value of codon positions as in A, from a yeast ribosome profiling library we constructed using CircLigase II as described by M$^c$Glincy and Ingolia[29]. e, f, Contributions from (e) codon position −5, at the 5' ends of footprints, and (f) the A site, in human ribosome profiling data[30] versus our yeast ribosome profiling data, both using CircLigaseII. Analysis was limited to 28-nt footprints to avoid frame biases. g, Ligation efficiency of CircLigase II. Oligonucleotide substrates resembling ribosome footprints at the circularization step of the protocol, with different three-nucleotide end sequences, were ligated by both enzymes. Circularization was assayed by qPCR using primers spanning the ligation as compared to primers in a contiguous region of the oligo. Ligation was calculated relative to CircLigase I ligation of the best-ligated substrate. Each point represents the ratio of the means of three qPCR replicates; error bars represent the standard error of that ratio.

FIGS. 4A-D. Design of synonymous sequences shows elongation rate affects translation output, a, Six reporter constructs with distinct synonymous eCitrine coding sequences were inserted into the his3Δ1 locus of BY4742 yeast, and an equivalent construct with a constant mCherry coding sequence was inserted into the his3Δ1 locus of BY4741 yeast. The haploids were mated to produce diploid yeast with both reporters, whose fluorescence was then measured with flow cytometry. b, The synonymous eCitrine sequences included the fastest and slowest predicted sequences under our model (magenta and red), plus sequences with predicted translation elongation times at the 0th, 33rd, 67th, and 100th percentiles of a randomly generated set of 100,000 synonymous eCitrine sequences (blue, green, yellow, and orange, respectively). The score distribution of 100,000 random eCitrine sequences is shown in lavender. The scores of endogenous yeast genes, rescaled by length to compare with eCitrine, are shown in gray. c, eCitrine:mCherry fluorescence ratio, as measured by flow cytometry of 11,000-18,000 yeast, versus the predicted elongation time of each sequence. Each + symbol represents the median ratio of yellow and red fluorescence from one biological replicate of the given eCitrine strain. Eight biological replicates, each an independent integration of the reporter construct, are included for each strain, except for the strains shown in blue and orange, which have seven, and the strain shown in green, which has three. Colors as in (b). d, Translation efficiency, or median eCitrine:mCherry fluorescence ratio divided by relative eCitrine:mCherry mRNA ratio (ratio of medians of three qPCR replicates), for each eCitrine variant, versus the predicted elongation time of each sequence. Purple, yECitrine sequence; other colors as in (b). Each point represents one biological replicate of the given eCitrine strain; three biological replicates were measured for each strain except two for the strain shown in red.

Figure 5B:
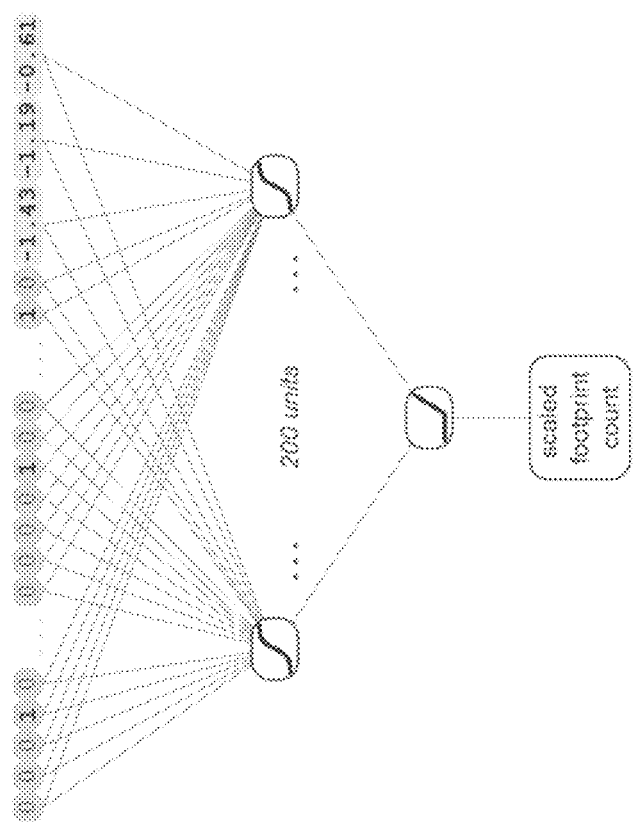
Figure 5A:
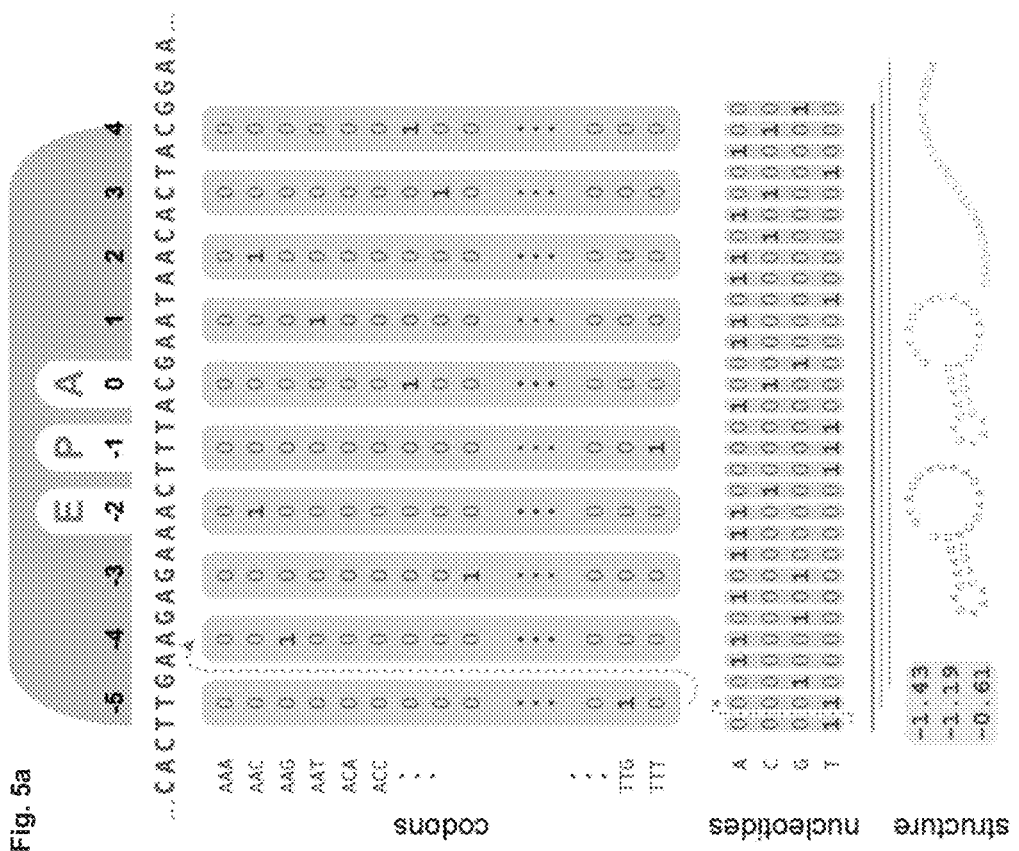

FIG. 5A-B. Neural network model structure. (A) Counts are predicted at the A site codon. In the model shown, a sequence neighborhood spanning from 5 codons upstream of the A site (codon −5) to 4 codons downstream of the A site (codon +4) is used as the predictive region. This neighborhood is divided into codons and encoded via one-hot encoding (purple) for input into a regression model. We also encode the same region as nucleotide features (green) and include these features in the model. Finally, we compute RNA structure scores on three 30 nt sliding structure windows that span the width of a typical 28 nt footprint. These windows start 17, 16, and 15 nucleotides before the start of the A site. (B) These features are concatenated in a vector, which is used as the input to a fully connected feedforward neural network model. Each model in this paper contains one hidden layer with 200 hidden units, and a tanh activation function on the hidden units. The output layer contains one unit with a ReLu activation function to enforce nonnegativity of predicted scaled counts. Depicted sequence:

(SEQ ID NO. 3)
CACTTGAAGAGAAACTTTACGAATAACACTACGGAA

Figure 6:
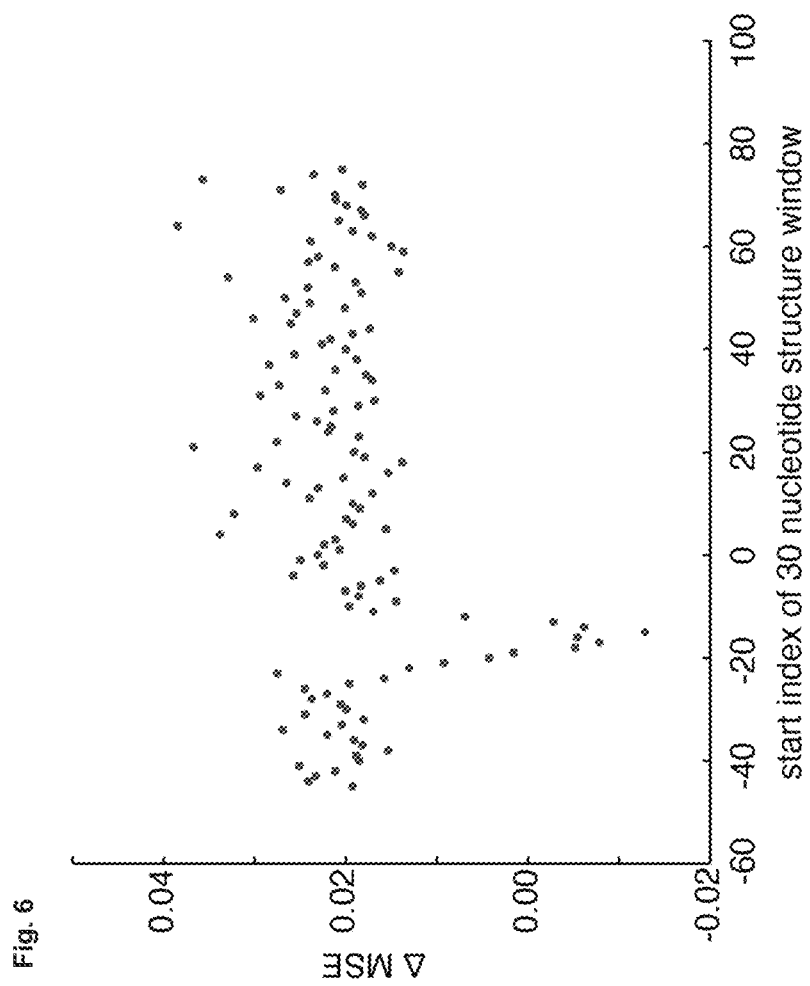

FIG. 6. Change in MSE upon including mRNA structure, comparing the performance of a model using a sequence neighborhood from codons −7 to +5 against models that each also include the folding energy of a single 30 nt window. Each point shows the change in MSE upon including a particular window. The greatest improvement in MSE is achieved by including a window starting at nucleotide position −17 and ending at position 12. This is roughly coterminal with a typical 28 nt ribosome footprint (nucleotide positions −15 to +12).

Figure 7A:
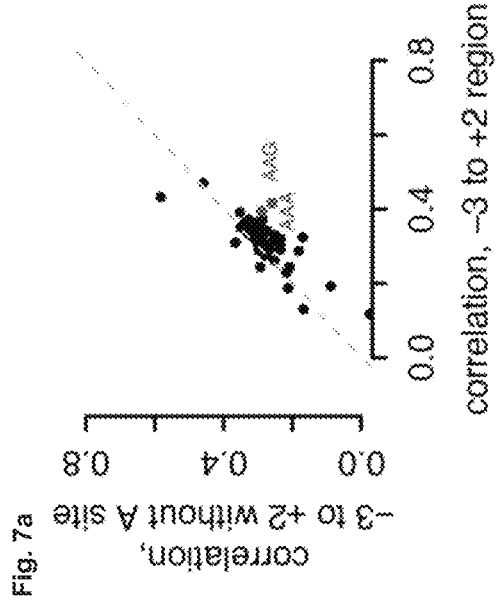
Figure 7B:
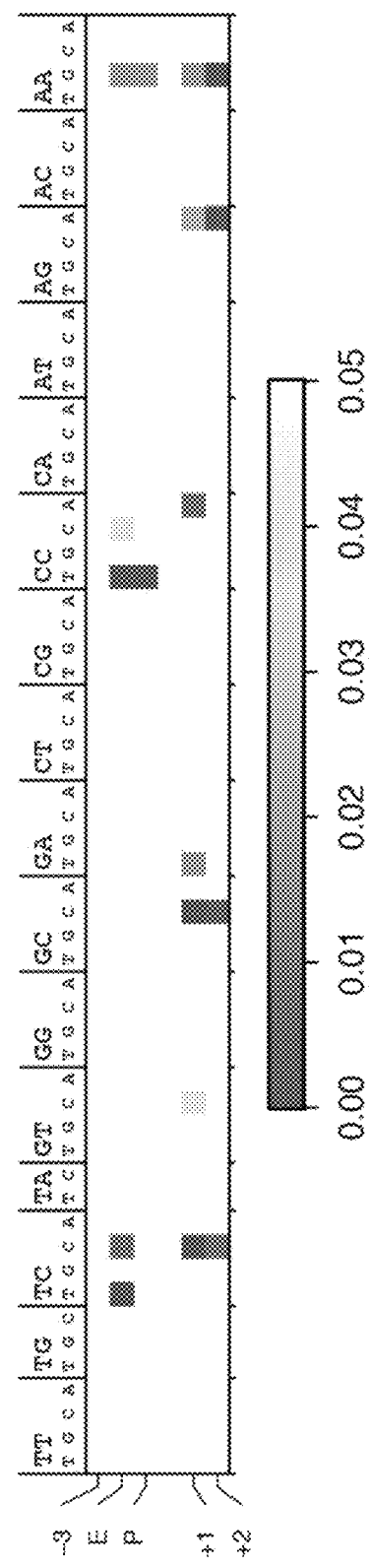

FIGS. 7A-B. Relative contributions of A site codons and context. (A) Pearson correlation of observed vs. predicted scaled counts per codon, for a model using codons −3 to +2 and associated nucleotides (x-axis) and a model using the same region but without the A site (y-axis). Codons whose inclusion in the model leads to significantly better prediction (higher correlation between the observed and predicted scaled counts), per a t-test of the Fisher transformation of correlations with an FDR of 5%, are shown in red. (B) We extracted the sequence context (codons −3 to +2) for all positions where the squared error was higher for an A-site-only model than for a model with codons −3 to +2 but no A site. The proportion of codons at each position in this set was compared to the overall distribution of codons in the test set with a two-sided proportion test, using an FDR of 5%, and codons with adjusted p<0.05 are shown in the plot. Depicted sequence:

(SEQ ID NO. 4)
TGCATGCTGCATCTGCATGCATGCATGCATGCATGCATGCATGCAT
GCATGCATGCA.

Figure 8A:
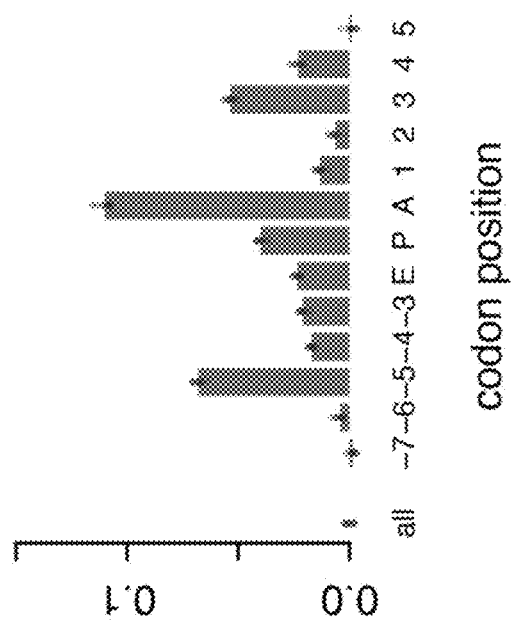
Figure 8B:
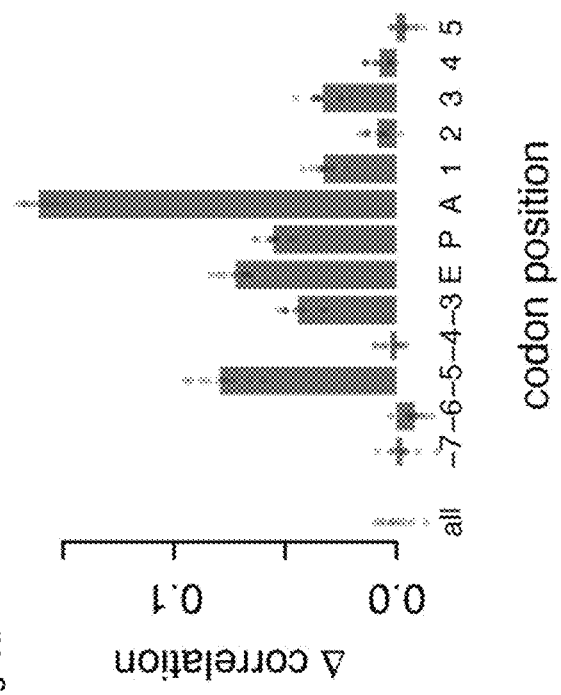

FIGS. 8A-B. Predictive value of codon positions. Predictive value of codon positions in (A) a human ribosome profiling data set using Circligase 11 (Iwasaki, S. et al., Nature. 534(7608), 558-61, 2016), and (B) a yeast ribosome profiling dataset using Circligase I (Schuller, A. et al., Mol. Cell. 66, 194-205.e5, 2017). As in FIG. 3A, we trained a reference model on codons −7 to +5 (with nucleotide features over the same neighborhood), and then a series of leave-one-out models each excluding exactly one codon in the sequence neighborhood, along with the corresponding nucleotides. For each model, we compute Pearson correlations between the true and predicted scaled counts over all codons in the test set. Shown is the difference in Pearson correlations between the reference model and the leave-one-out models. Higher Δr indicates increased importance of that codon position to model predictions.

Figure 9A:
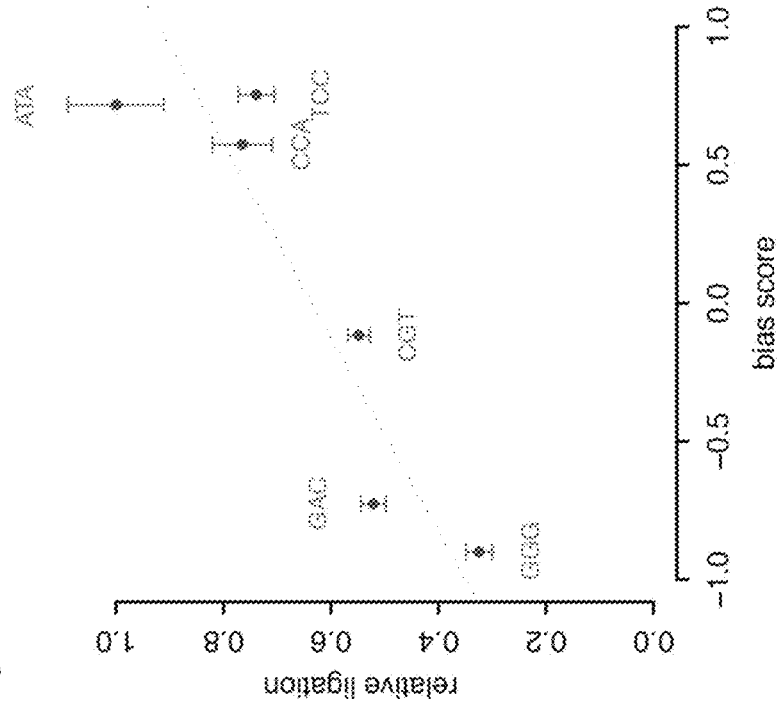
Figure 9B:
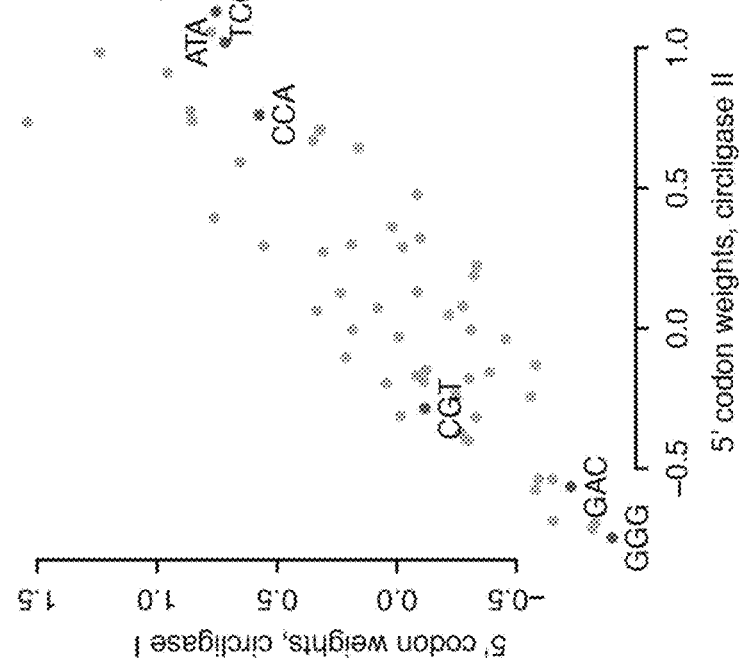

FIGS. 9A-B. Circligase I and II preferences. (A) Mean contributions to scaled counts at the 5' end of a ribosome footprint, for yeast data sets generated with Circligase II (our data) and Circligase I (Schuller, A. et al., Mol. Cell. 66, 194-205.e5, 2017). Scores are from the −5 codon position. To generate these scores, we trained models only on 28 nt footprints with their 5' end aligning with the beginning of the −5 codon. (B) Ligation efficiency of CircLigase I enzyme, as in FIG. 3G.

FIG. 10. Flow cytometry gating strategy. Scatter plot of forward scatter area (FSC) against side scatter area (SSC, arbitrary units) for each of the 50000 events collected for a representative flow cytometry sample of diploid yeast expressing mCherry and a differentially optimized eCitrine. Events are colored by their density on the plot, low density points being colored blue moving to high density events being colored dark red. Events outside the plotted area are denoted by grey lines at the edge of the plot. Annotated by red regions are seven areas of high local density defined by the curv2filter method, each with the number of events they contain. For each sample, events within the most populous region were taken forward for further analysis; in this representative sample, these would be the events within Area 3.

Figures 11A, 11B:
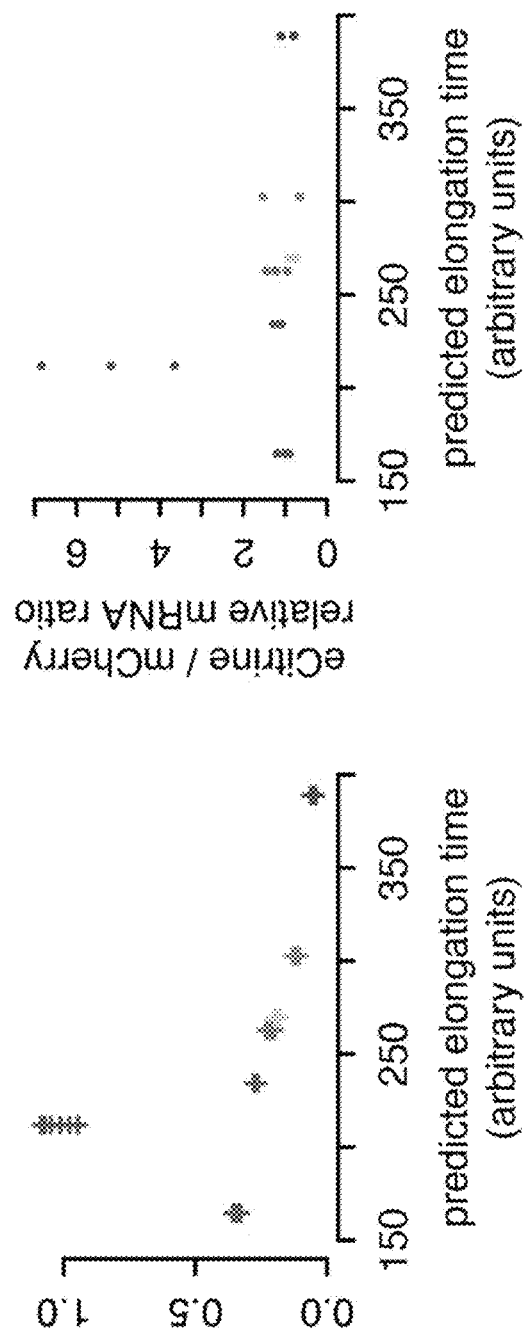

FIGS. 11A-B. yECitrine mRNA level and fluorescence. (A) eCitrine:mCherry fluorescence ratio as in FIG. 3C, including this ratio for the yECitrine sequence (magenta). (B) eCitrine:mCherry mRNA ratio measured by qPCR in biological replicates of four strains (colors as in FIG. 4). Each data point represents the ratio of medians of three technical replicates, normalized to the median ratio of the highest expression strain.

DESCRIPTION OF PARTICULAR
EMBODIMENTS OF THE INVENTION

Unless contraindicated or noted otherwise, in these descriptions and throughout this specification, the terms "a" and "an" mean one or more, the term "or" means and/or.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Method Overview

A. Measure Translation in Organism of Interest

Translation of genes into protein is carried out by the ribosome, a large and sophisticated cellular machine. The ribosome decodes each 3-nt codon in the messenger RNA (mRNA) and adds each specified amino acid to the new protein chain. Ribosome profiling can measure translation by capturing the positions of all ribosomes in a sample of cells. Cellular mRNA is cleaved by enzymes, leaving only the fragments of mRNA that are physically protected by ribosomes. The ribosome-protected mRNA fragments, which are 20-30 nucleotides long, are then sequenced using an Illumina sequencer (or equivalent) and counted. The number of fragments originating from each gene shows how much protein is being made from that gene. Further, the distribution of fragments along the gene shows how quickly or slowly the ribosome is moving at each position. Ribosomes spend more time sitting on slowly-translated codons, and so fragments from those positions will be captured and sequenced more frequently. Thus, the number of fragments can show which sequences are translated more efficiently.

In our method, we first conduct a ribosome profiling experiment in the organism or tissue of interest using methods similar to those described by Ingolia et al, 2009.

B. Learn Sequence Preferences for Translation

We then use the counts of fragments at each position to learn the organism's sequence preferences for fast translation. We count how many ribosomes are seen at each codon position in each gene, normalized by the average number of ribosomes per position in that gene. We then use machine learning methods to learn a model for the position→normalized count relationship of the whole genome. We encode a 30-40 nucleotide window around each codon as a binary feature vector, and we train neural networks and ordinary least squares (OLS) models to predict normalized counts as a function of these features. The result is a model that can take as input any arbitrary gene sequence and predict how ribosomes will slow down or speed up on that sequence.

C. Predict the Best Codon Sequence to Encode a Given Protein Sequence

Finally, we take that model and use it to design an optimized sequence to encode a given protein. We use a dynamic programming algorithm to find the optimal codon sequence in the set of synonymous sequences that code for the protein. To simplify in this example, we assume that our model uses a 10 codon neighborhood as input features, and each amino acid has four possible codons.

(i) Score all 1,048,576 possibilities for the first 10 codons of a protein with a fixed amino acid sequence, c0 . . . c9, and save these values as the cumulative score.

(ii) Iterating over i in {1, 2, . . . length of sequence in codons −10}

A. For each 9-codon suffix $c(i)$ . . . $c(i+8)$, store a pointer to the best of the 4 possible choices for codon $c(i-1)$, and save the score of that $c(i-1)$ . . . $c(i+8)$ window.

B. Then generate each $c(i)$ . . . $c(i+9)$ sequence you get by appending any possible choice for the next codon, $c(i+9)$, to our set of 9-codon suffixes $c(i)$ . . . $c(i+8)$, and score those new 1,048,576 10-codon sequences. For each new sequence $c(i)$ . . . $c(i+9)$, store a pointer to the previous $c(i-1)$ . . . $c(i+8)$ sequence with the best cumulative score. Add the score of the previous sequence to the score of the current $c(i)$ . . . $c(i+9)$ sequence.

(iii) After iteration we have a scoring table that is 1,048,576×the length of your protein, with each cell in a column of the table containing a pointer back to the best sequence to have come before the current position.

(iv) At the end, choose the best cumulative score at over all sequences at the last position, and trace back to the first position to reconstruct the optimal sequence.

To implement this method, one would conduct ribosome profiling in an organism or cell type of interest, train the translation speed model on the ribosome profiling data, predict an optimized DNA codon sequence for the fixed protein sequence of interest, then synthesize that DNA sequence and introduce it into the organism.

The method has been reduced to practice, including using translation data from yeast. We trained a single-layer feed-forward neural network then implemented the optimization method in python and predicted an optimized sequence for green fluorescent protein (GFP). GFP is a string of 238 amino acids encoded by a gene sequence of 714 nucleotides. The protein begins with methionine-serine-lysine-glycine-glutamate (MSKGE). In the organism from which natural GFP was isolated, Aequorea victoria, the first amino acids are encoded as ATG-AGT-AAAGGA-GAA (SEQ ID NO. 5). But there are six possible codons for serine, two for lysine, four for glycine, and two for glutamate, and our method predict that the protein will be expressed more efficiently in yeast if it is encoded with different serine and glycine codons: ATG-TCC-AAA-GGT-GAA (SEQ ID NO. 6). We are synthesizing artificial gene sequences to encode GFP with this optimized sequence in yeast, and we will compare fluorescence levels between the natural and optimized versions.

Our method has major strengths over existing methods including:

It is empirical and based on direct measurements. Existing methods rely on counting the frequency of each codon in a genome, rather than looking at actual translation data, to observe the supposed preferred codons. The codon count is not actually an accurate measure of how efficiently that codon is translated.

It considers more information than solely the 3-nucleotide sequence being translated. By considering a window of −30 nucleotides around the site of translation, we incorporate more information about how the ribosome interacts with its substrate.

As a result, our predicted optimized sequences differ from published sequences that are widely used as 'optimized' sequences. The published sequence of GFP for expression in yeast is different than the optimized sequence we describe above, using different serine, glycine, and glutamate codons: ATG-TCA-AAA-GGC-GAG (SEQ ID NO. 7).

(SEQ ID NO. 7)
ATG-TCA-AAA-GGC-GAG.

Another strength of our method is that it can capture differences in translation in different conditions or in different tissues within the same organism, by using ribosome profiling data collected from the conditions or tissues that are most relevant. Recent research has shown that codon preferences vary between conditions even within the same organism, based on changes to tRNA availability and other factors.

At any given moment a ribosome is decoding one 3-nucleotide codon, which is positioned in the A site of the ribosome. A tRNA comes into the A site, matches the codon, and adds the correct amino acid.

Discussion

In our method we take empirical data from ribosome profiling (U.S. Pat. No. 8,486,865), that measures the dwell time of ribosomes on each position of each mRNA. We use those measurement as machine learning input to determine how a particular sequence determines how quickly ribosomes move, and then we use inferred rules to design sequences for expression at high, low, or intermediate levels. We established that a window of sequence near the codon being decoded was a good predictor of ribosome speed and that ribosome speed was a good predictor of protein output. Our method does not need to know how the particular biochemical features of that sequence cause the speed differences. Instead, we form an empirical measure based on data. Thus, our method can be used to learn the empirical preferences in any particular setting, by doing a ribosome profiling experiment—translation conditions can be quite different between different organisms, and in different cell types.

Our method is innovative over related concepts. For example, WO2016112142, "Modeling ribosome dynamics to optimize heterologous protein production", employs a conceptually different approach, starting with specific sequence features that are expected to make a difference. The features include the strength of interaction of the ribosomal RNA with a region of mRNA sequence behind the codon that is being translated and a model of how the force of this interaction leads to partial ribosome displacement off the A site codon. They use these, combined with existing measurements of tRNA abundance, to make an explicit model of ribosome dynamics, and then use that model to design sequences for faster translation.

Our method, which learns relevant features in an unbiased way, picks up features outside of the ones considered by WO2016112142. Their method does, in effect, use a window of sequence near the A site, like our method, but it only evaluates one aspect of this window (rRNA:mRNA pairing, which, again, is not an idea that is widely accepted in eukaryotes, and is under some debate in prokaryotes).

Because our method uses empirical measurements of ribosome dwell time from ribosome profiling, we do not need to rely on tRNA abundance measurements (which are hard to obtain, and not available for many organisms/conditions) nor limit ourselves to genome-wide codon preferences as a proxy to tRNA abundance. Instead, we can learn the sequence preferences from real data—our model will inherently reflect tRNA abundance only to the extent that it matters for translation. We do not need to know the actual tRNA abundance, and we do not need to know how much it matters.

Notably ours is the first method for designing sequences that does not rely on some pre-existing measure of tRNA abundance/tRNA availability/codon preference. And, because those tRNA contributions aren't well known, that makes our method more accurate and more flexible.

Inventive aspects of our method include:
  using an mRNA sequence window around a codon to predict its translation, without requiring knowledge of the specific biochemical properties responsible for the effect (this does not depend on specific implementation—could be a neural network, linear regression, etc)
  use of a neural network to learn the effect of a specific mRNA sequence window on translation
  use of a neural network to score/predict the translation of any existing or novel sequence
  specific method of optimizing a sequence for highest or lowest translation using that
  neural network score
  randomly generating many sequences and scoring them to design sequences for translation at specific intermediate levels Example: Accurate Design of Translational Output by a Neural Network Model of Ribosome Distribution Synonymous codon choice can have dramatic effects on ribosome speed and protein expression. Ribosome profiling experiments have underscored that ribosomes do not move uniformly along mRNAs. We modeled this variation in translation elongation using a feedforward neural network to predict the ribosome density at each codon as a function of its sequence neighborhood. Our approach revealed sequence features affecting translation elongation and characterized large technical biases in ribosome profiling. We applied our model to design synonymous variants of a fluorescent protein spanning the range of translation speeds predicted with our model. Levels of the fluorescent protein in budding yeast closely tracked the predicted translation speeds across their full range. We therefore demonstrate that our model captures information determining translation dynamics in vivo, that we can harness this information to design coding sequences, and that control of translation elongation alone is sufficient to produce large, quantitative differences in protein output.

Introduction

As the ribosome moves along a transcript, it encounters diverse codons, tRNAs, and amino acids. This diversity affects translation elongation and, ultimately, gene expression. For instance, exogenous gene expression can be seriously hampered by a mismatch between the choice of synonymous codons and the availability of tRNAs. The consequences of endogenous variation in codon use have been more elusive, but new methods have revealed that synonymous coding mutations, upregulation of tRNAs, and mutations within tRNAs can have dramatic effects on protein expression, folding, and stability[1-3]. Codon usage can directly affect the speed of translation elongation[4]. However, translation initiation has been considered the rate-limiting step in translation, implying that changes in elongation speed should have limited effects[5]. Recent work has suggested a relationship between codon use and RNA stability; slower translation may destabilize mRNAs and thus decrease protein expression[6,7]. These opposing viewpoints have yet to be fully reconciled, leaving us with an incomplete understanding of what defines a favorable sequence for translation.

With the advent of high-throughput methods to measure translation elongation in vivo, we can understand the functional implications of codon usage. Ribosome profiling measures translation transcriptome-wide by capturing and sequencing the regions of mRNA protected within ribosomes, called ribosome footprints[8]. Each footprint reflects the position of an individual ribosome on a transcript, and we can reliably infer the A site codon—the site of tRNA decoding—in each footprint (FIG. 1a). This codon-level resolution yields the distribution of ribosomes along mRNAs from each gene. We can use the counts of footprints on each codon to infer translation elongation rates: slowly translated codons yield more footprints, and quickly translated codons yield fewer (FIG. 1b). Analyses of ribosome profiling data have shown a relationship between translation elongation rate and biochemical features like tRNA abundance, wobble base pairing, amino acid polarity, and mRNA structure[9-18]. Expanded probabilistic and machine learning models have shown that the sequence context of a ribosome contributes to its elongation rate, both directly and through higher order features such as nascent protein sequence[15-17,19]. Computational modeling has also indicated that technical artifacts and biases contribute to the distribution of ribosome footprints[18-21]. However, it remains a challenge to distinguish experimental artifacts from the biological determinants of elongation rate. Here, we have used neural networks to model ribosome distribution along transcripts. The model captured both biological variation in translation elongation speed and technical biases affecting footprint count, which we confirmed experimentally. We have implemented a tool, Iχnos, that applies our model to design coding sequences, and used this to design sequences spanning a range of predicted translation elongation speeds. We found that the predicted elongation speeds accurately tracked protein expression, supporting a role for the elongation phase of translation in modulating gene expression.

Design and Performance of a Neural Network Model of Translation Elongation

First, we developed a regression framework to model the distribution of ribosomes along transcripts as a function of local sequence features. As our measure of ribosome density on individual codon positions, we calculated scaled footprint counts by dividing the raw footprint count at each codon position by the average footprint count on its transcript (FIG. 1b). This normalization controls for variable mRNA abundances and translation initiation rates across transcripts. The scaled count thus reflects the relative speed of translation elongation at each position. We used a sequence neighborhood around the A site as the predictive region for scaled counts, and encoded this neighborhood as input to a regression model via one-hot encoding of the codons and nucleotides in this region (FIG. 5). Then we learned a regression function with a feedforward neural network, trained on a large, high quality ribosome profiling data set from *Saccharomyces cerevisiae*[22]. We chose the top 500 genes by footprint density and coverage criteria, and sorted these into training and test sets of 333 and 167 genes, respectively.

We determined the sequence neighborhood that best predicted ribosome density by comparing a series of models ranging from an A-site-only model to a model spanning codon positions −7 to +5 (FIG. 1c). The identity of the A site codon was an important, but limited, predictor of the distribution of ribosome footprints (Pearson's r=0.28). Expanding the sequence context around the A site steadily improved the predictive performance, up to the full span of a ribosome footprint (codons −5 to +4). Additional sequence context beyond the boundaries of the ribosome did not improve performance. We also observed a large boost in predictive performance by including redundant nucleotide features in addition to codon features over the same sequence neighborhood, especially near the ends of the ribosome footprint (FIG. 1c, r=0.53 for −5 to +4 model including nucleotide features, $\Delta r$=0.08 relative to no-nucleotide model). Linear regression models that only included codon features performed similarly to the neural networks we tested, but they did not improve with the inclusion of nucleotide features. This indicates that the neural network models learn a meaningful and nonlinear predictive relationship in nucleotide features, particularly toward the flanking ends of footprints, that makes them more successful than linear models.

Next we assessed the contribution of local mRNA structure to footprint distributions. We computed mRNA folding energies in sliding 30 nt windows over all transcripts, and trained a series of models that each included one window from nucleotide positions −45 to +72 relative to the A site. Performance improved upon including structure scores at nucleotide positions −17, −16, and −15, i.e., the windows that span the actual ribosome footprint ($\Delta r$=0.03; FIG. 1c and FIG. 6). No individual windows downstream of the footprint improved our predictions, and the maximum structure score over 30 sliding windows downstream of the ribosome had only a slight effect ($\Delta r$<0.01) (FIG. 1c). Thus, our approach does not capture a conclusive effect of downstream mRNA structure on elongation rate. We were surprised to see an effect of structure within the ribosome, so we tested the direction of the effect and found that more structure in these windows led to lower predicted footprint counts. This indicates that stable mRNA structure in the footprint fragments themselves is inhibiting their in vitro recovery in ribosome profiling experiments, and our model is capturing the bias that this introduces to the data.

Our best model incorporated a sequence window from codons −5 to +4 represented as both codons and nucleotides, as well as structure features of the three windows spanning the footprint. It captured sufficient information to accurately predict footprint distributions on individual genes (FIG. 1e), and yielded a correlation of 0.57 (Pearson's r) between predicted and true scaled counts over all positions in the test set (FIG. 1d). Although our model performed well across a range of scaled counts, it had difficulty predicting very high scaled footprint counts at a small number of sites. These sites may represent ribosome stalling that is determined by biological factors encoded outside of this local sequence neighborhood[16].

Our model was trained on highly expressed genes because abundant ribosome footprints enable more accurate sampling of ribosome positions. However, highly expressed genes can have biased codon usage[23]. To ensure that our model was accurately predicting translation on genes across the full range of expression and codon usage, we computed the correlation between the observed and predicted scaled counts for all yeast genes. Performance decreased with lower expression (FIG. 2a), but we hypothesized that the decreased performance reflected noisier observed footprint counts arising from less-abundant mRNAs, rather than differences in their codon composition. To test this, we downsampled the footprints for each of the 1000 highest-expression genes to match the average counts per codon of the 1000th gene, and repeated this procedure for the top 2000, 3000, and 4000 genes. We then compared the predictions of our model, which had been trained on the full data from highly expressed genes, against the downsampled data. At each coverage level, our method performed equally well on high-expression genes and low-expression genes. Thus, our model had no decrease in performance on genes that tend to have less favored codon content, after controlling for data density.

We also compared the performance of our model against two earlier approaches that incorporate information from the sequence neighborhood of each codon to predict ribosome distributions: RUST, which computes the expected ribosome density at each codon based on its sequence window[19], and riboshape, which uses wavelet decomposition to denoise the observed counts by projecting them into different subspaces at different levels of resolution (smoothness), and then predicts ribosome density after transformation into these subspaces[15]. To compare riboshape to our own method and to RUST, we evaluated how well its predictions in the highest resolution subspace (i.e., closest to the raw data) correlated with the observed footprint counts. Our model out-performed both models, with an average Pearson correlation per gene of 0.56 versus 0.48 (RUST) and 0.41 (riboshape) across all genes that were included in all three analyses (FIG. 2b). We also found that our predictions of the raw data were better than riboshape's predictions of the transformed data at each resolution (Supplementary Table 1).

Sequences Near the a Site and at the Ends of Footprints Contribute to Footprint Density To quantify the influence of distinct positions in the sequence neighborhood on elongation rate, we trained a series of leave-one-out models that excluded individual codon positions from the input sequence neighborhood, and compared their performance to a reference model that included all positions. We found that the A site codon contributed the most to predictive performance ($\Delta r$=0.13), but we also saw contributions from the surrounding sequence context, including the P and E sites ($\Delta r$=0.03 and 0.03) (FIG. 3a). Each codon position from −5 to +4, the span of a typical 28 nt ribosome footprint, improved performance of the full model, whereas positions outside the span of a footprint decreased performance. Contributions from the E and P sites suggest that the continued presence of tRNAs at these positions modulates elongation rate. In contrast, the large contribution of the +3 codon ($\Delta r$=0.06), at the 3' end of the footprint, likely reflects artifactual biases arising from the ribosome profiling process, corroborating previous reports of fragment end biases[19,20].

We were also interested in understanding the relative influence of the A site codon and its immediate environment. Overall, the A site codon and its immediate environment predict ribosome density similarly well (Pearson's r=0.28 for the A site only, r=0.26 for the codons from −3 to +2 excluding the A site). To identify A-site codons that tend to dominate the prediction, contributing relatively more than their context, we compared the performance of a −3:+2 model and a model with codons −3 to +2 but excluding the A site (FIG. 7). We found that the presence of lysine codons AAA and AAG in the A site led to the strongest predictions, in agreement with a major effect of charged lysine residues on translation[11]. Conversely, we also identified a number of sequence contexts that tended to dominate the prediction, by looking at the sequence contexts of the positions with higher squared error arising from the A-site-only prediction at that position than the no-A-site context (FIG. 7).

Next, we examined what our model had learned about the relationship between sequence and ribosome density. The raw parameters of a neural network can be difficult to interpret, so we determined a score for each codon at each position by computing the mean increase in predicted scaled counts due to that codon (FIG. 3b). Time spent finding the correct tRNA is considered to be a main driver of elongation speed, and consequently footprint counts[24]. Indeed, the A site codon scores exhibited the widest range of codon scores, and scores at this position but not other positions correlated with tRNA Adaptation Index (tAI), a measure of tRNA availability[25], as has been widely observed (Pearson's r=0.50; p=0.0005 after Bonferroni correction). Our results highlighted the well-characterized slow translation of CCG (Pro), CGA (Arg), and CGG (Arg) codons at the A site[26]. Our data also underscore that sequences in the P site contribute to elongation speed. The CGA codon showed a particularly strong inhibitory effect in the P site, in keeping with recent results[26,27]. We noted that this codon forms a disfavored I:A wobble pair with its cognate tRNA, distorting the anticodon loop[28], while the four fastest P site codons all form I:C wobble pairs (FIG. 3c). Overall, I:C base pairs in the P site contributed to faster translation (Mann-Whitney p=0.014 after Bonferroni correction, FIG. 3c). From this, we concluded that the conformation of the tRNA:mRNA duplex can influence its passage through the ribosome, not just initial recognition in the A site.

We also observed strong sequence preferences at the 3' end of ribosome footprints. Sequence bias has previously been noted in the 5' and 3' ends of ribosome footprints, and this bias has been suggested to arise from ligase preferences during library preparation[19,20]. To compare features of ribosome profiling data generated in different experiments, we applied our model to a large ribosome profiling dataset that we generated from yeast using a standard ribosome profiling protocol[29]. Models trained on these data learned disconcertingly high weights for both the −5 and +3 codon positions (FIG. 3d). The −5 codon, i.e., the 5' end of a footprint, was the single strongest predictor of footprint counts, exceeding even the A site. We found similarly large 5' end contributions in published yeast and human datasets generated using similar protocols[30,31] (FIG. 8). These experiments, like our own, made use of CircLigase enzymes to circularize ribosome footprints after reverse transcription. In contrast, the experiment we first modeled used T4 RNA ligase to attach 5' linkers directly onto ribosome footprint fragments[22]. To compare end sequence preferences between experiments, we trained models on only 28-nt footprints so that the ends of the footprints corresponded to the −5 codon position. Comparing the T4 ligase yeast data with CircLigase yeast data[31], we observed no relationship between the scores learned at 5' footprint ends (r=0.05), but a high correlation between scores at the A site, where we would expect biological similarity (r=0.86). In contrast, we observed a high correlation at the −5 position between our CircLigase yeast data and the CircLigase-generated human data set[30] (r=0.83, FIG. 3e), but no significant relationship at the A site, where we would expect species-specific codon bias (r=−0.21, p=0.11, FIG. 3f). This suggested that the fragment end scores reflected experimental artifacts rather than in vivo biology.

To directly test the impact of enzyme biases on recovery of ribosome-protected fragments, we experimentally measured the ligation of synthetic oligonucleotides with end sequences shown to be favored or disfavored in our model. The relative ligation efficiency of each substrate closely mirrored the end sequence scores learned by our model for both CircLigase I and CircLigase II (FIG. 3g and FIG. 9). The least-favored sequences were ligated by CircLigase II with only 20% the efficiency of the most-favored sequences, meaning that some ribosome footprints would be represented at five times the frequency of other footprints for purely technical reasons. This biased recovery of fragments could skew the results of ribosome profiling experiments, affecting estimates of elongation and overall per-gene translation.

Expression of Synonymous Reporters Closely Tracks Predicted Translation Speeds

Our model captured the quantitative preferences of ligases for footprint end sequences and established that a substantial portion of the predictive information of these end regions is due to technical artifacts. However, the biologically sensible weights learned for codons in the A site showed that the model captured substantial biology as well. We reasoned that, if our model were capturing biological aspects of translation elongation, we could use the parameters learned by the model to design sequences that would be translated at different rates. We relied on the information found in the codons closer to the A site, to focus on the biological contributions and reduce the influence of biases from the ends of footprints (discussed further in Supplementary Note 1).

Figure 4B:
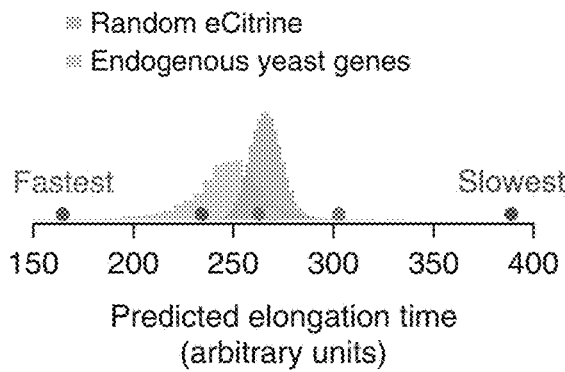

To test our model's ability to predict translation, we expressed synonymous variants of the yellow fluorescent protein eCitrine in yeast (FIG. 4a). First, using the yeast ribosome profiling data from Weinberg et al., we trained a neural network model with a sequence neighborhood extending from codon positions −3 to +2. Next, we designed a dynamic programming algorithm to compute the maximum- and minimum-translation-time synonymous versions of eCitrine based on our model. We defined the overall translation time (in arbitrary units) of a gene as the sum of predicted scaled counts over all codons in the gene. We also generated and scored a set of 100,000 random synonymous eCitrine CDSs and selected the sequences at the 0th, 33rd, 67th, and 99th percentiles of predicted translation time within that set (FIG. 4b). We used flow cytometry to measure the fluorescence of diploid yeast, each containing an eCitrine variant along with the red fluorescent protein mCherry as a control, and calculated relative fluorescence of each variant (FIG. 4c, FIG. 10).

Figure 4C:
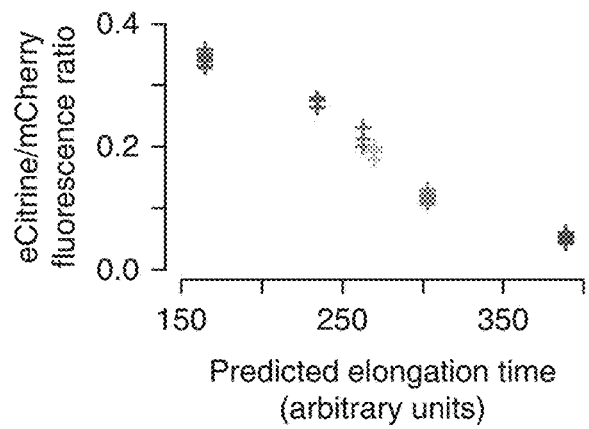
Figure 4D:
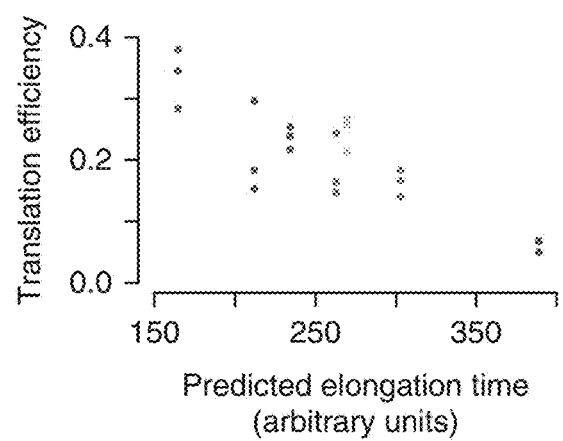

The expression of eCitrine in each yeast strain closely tracked its predicted elongation rate, with the predicted fastest sequence producing six-fold higher fluorescence than the predicted slowest sequence (FIG. 4c). However, the existing yeast-optimized yECitrine sequence[32] produced three-fold higher fluorescence than our predicted fastest sequence (FIG. 11). To understand the source of this discrepancy, we measured eCitrine mRNA from all strains and found that sequences designed by our method had approximately equivalent mRNA levels, while yECitrine had five-fold more mRNA (FIG. 11). Calculating translation efficiencies, or protein produced per mRNA, reconciled this disagreement. We observed a clear linear relationship between predicted elongation rate and translation efficiency (FIG. 4d)

Discussion

These experiments demonstrate that our model is able to predict large, quantitative differences in protein production, based only on information about translation elongation. The sequences we designed and tested have predicted translation speeds that span the range of natural yeast genes (FIG. 4b). This supports an effect of elongation rate on the translation efficiency and protein output of endogenous genes. Initiation rather than elongation is usually thought to be rate limiting for protein production of most endogenous genesu[24]. Models have suggested that highly expressed trans-genes might deplete the effective supply of ribosomes, lowering initiation and thus causing elongation to be rate-limiting, but our reporter is expressed at the level of many endogenous genes and should represent well under 1% of mRNA. Although codon choice can also affect mRNA stability and thus total protein output[6,7], our fast and slow predicted sequences have equivalent steady-state mRNA. Further, an effect arising purely from mRNA stability would affect protein output but not translation efficiency, counter to our observations. Instead, our results indicate that optimized elongation rates do result in more protein per mRNA, and this does not depend entirely on mRNA stability. Our approach can capture empirical information about codon preferences in any system where translation can be measured by ribosome profiling, and apply it to design sequences for quantitative expression in that system.

Data Availability

Ribosome profiling sequence data generated for this study have been deposited in NCBI GEO as accession GSE106572. All Iχnos software and analysis scripts, including a complete workflow of analyses in this paper and all analyzed data used to create figures, can be found at https://github.com/lareaulab/iXnos.

Ribosome Profiling

Yeast ribosome profiling was performed exactly according to M$^c$Glincy & Ingolia[29] with the following modifications:

250 mL of YEPD media was inoculated from an overnight culture of BY474 to an OD600 of 0.1. Yeast were grown to mid-log phase and harvested at an OD600 of 0.565. Lysis proceeded according to M$^c$Glincy & Ingolia[29] except with no cycloheximide in the lysis buffer (20 mM Tris pH 7.4, 150 mM NaCl, 5 mM MgCl2, 1 mM DTT, 1% v/v Triton X-1000, 25 U/ml Turbo DNase I). To quantify RNA content of the lysate, total RNA was purified from 200 μL of lysate using the Direct-zol RNA MiniPrep kit (Zymo Research) and the concentration of RNA was measured with a Nano-Drop 2000 spectrophotometer (ThermoFisher).

Lysate containing 30 μg of total RNA was thawed on ice and diluted to 200 g±L with polysome buffer with no cycloheximide (20 mM Tris pH 7.4, 150 mM NaCl, 5 mM MgCl2, 1 mM DTT). 0.1 μl (1 U) of RNase I (Epicentre) was added to the diluted cell lysate and then incubated at room temperature for 45 minutes. Digestion and monosome isolation proceeded according to M$^c$Glincy & Ingolia[29], except with no cycloheximide in the sucrose cushion.

Purified RNA was separated on a 15% TBE/Urea gel, and fragments of 18-34 nt were gel extracted. Size was determined relative to RNA size markers NI-NI-800 and NI-NI-801[29] and NEB microRNA size marker (New England Biolabs). Library preparation proceeded according to MCGlincy & Ingolia[29]. The library was made with downstream linker NI-NI-811 (/5Phos/NNNNNAGCTAA-GATCGGAAGAGCACACGTCTGAA/3ddC/) (SEQ ID NO. 8) and a modified RT primer with a preferred CircLigase II substrate (AG) at the 5' end (oLFL075, 5'-/5Phos/AGATCGGAAGAGCGTCGTGTAGGGAAAGAG/iSp18/GTGACTGGAGTTCAGACGTGTGCTC) (SEQ ID NO. 9). Library amplification PCR used primers NI-NI-798 and NI-NI-825 (Illumina index ACAGTG). The resulting library was sequenced as single-end 51 nt reads on an Illumina HiSeq4000 according to the manufacturer's protocol by the Vincent J. Coates Genomics Sequencing Laboratory at the University of California, Berkeley.

Sequencing Data Processing and Mapping

A custom yeast transcriptome file was generated based on all chromosomal ORF coding sequences in orf_coding.fasta from the *Saccharomyces* Genome Database genome annotation R64-2-1 for reference genome version R64-1-1 (UCSC sacCer3) for *Saccharomyces cerevisiae* strain S288C. A human transcriptome file was generated from GRCh38.p2, Gencode v. 22, to include one transcript per gene based on the ENSEMBL 'canonical transcript' tag. For both human and yeast, the transcriptome file included 13 nt of 5' UTR sequence and 10 nt of 3' UTR sequence to accommodate footprint reads from ribosomes at the first and last codons. For yeast transcripts with no annotated UTR, the flanking genomic sequence was included. For human transcripts with no annotated UTR, or UTRs shorter than 13 or 10 nt, the sequence was padded with N.

Yeast ribosome profiling reads from Weinberg et al.[22] (SRR 1049521) were trimmed to remove the ligated 3' linker (TCGTATGCCGTCTTCTGCTTG (SEQ ID NO. 10) off of any read that ended with any prefix of that string, and to remove 8 random nucleotides at the 5' end (added as part of the 5' linker). Yeast ribosome profiling reads generated in our own experiments (GEO accession GSE106572) were trimmed to remove the ligated 3' linker, which included 5 random nucleotides and a 5-nt index of AGCTA (NNNN-NIIIIIAGATCGGAAGAGCACACGTCTGAAC) (SEQ ID NO. 11). Human ribosome profiling reads from Iwasaki et al.[30] (SRR2075925, SRR2075926) were trimmed to remove the ligated 3' linker (CTGTAGGCACCATCAAT) (SEQ ID NO. 12). Yeast ribosome profiling reads from Schuller et al.[31] (SRR5008134, SRR5008135) were trimmed to remove the ligated 3' linker (CTGTAGGCACCATCAAT) (SEQ ID NO. 13).

Trimmed fastq sequences of longer than 10 nt were aligned to yeast or human ribosomal and noncoding RNA sequences using bowtie v. 1.2.1.1[35], with options "bowtie -v 2-S". Reads that did not match rRNA or ncRNA were mapped to the transcriptome with options "bowtie -a --norc -v 2-S". Mapping weights for multimapping reads were computed using RSEM v. 1.2.31[36].

Assignment of A Sites

A site codons were identified in each footprint using simple rules for the offset of the A site from the 5' end of the footprint. These rules were based on the length of the footprint and the frame of the 5' terminal nucleotide. For each data set, the set of lengths that included appreciable footprint counts was determined (e.g. Weinberg 27-31 nt.). For each length, the counts of footprints mapping to each frame were computed. The canonical 28 nucleotide footprint starts coherently in frame 0, with the 5' end 15 nt upstream of the A site (citation). For all other lengths, rules were defined if footprints mapped primarily to 1 or 2 frames, and offsets were chosen to be consistent with over digestion or under digestion relative to a 28 nucleotide footprint. Footprints mapping to other frames were discarded.

Scaled Counts

For each codon, the raw footprint counts were computed by summing the RSEM mapping weights of each footprint with its A site at that codon. Scaled footprint counts were computed by dividing the raw counts at each codon by the average raw counts over all codons in its transcript. This controlled for variable initiation rates and copy numbers across transcripts. The resulting scaled counts are mean centered at 1, with scaled counts higher than 1 indicating slower than average translation. The first 20 and last 20 codons in each gene were excluded from all computations and data sets, to avoid the atypical footprint counts observed at the beginning and end of genes.

Genes were excluded from analysis if they had fewer than 200 raw footprint counts in the truncated CDS, or fewer than 100 codons with mapped footprints in this region. Then the top 500 genes were selected by footprint density (average footprint counts/codon). 2/3 of these genes were selected at random as the training set, and the remaining 1/3 of genes were used as the test set.

Input Features

The model accepts user defined sets of codon and nucleotide positions around the A site to encode as input features for predicting ribosome density. The A site is indexed as the 0th codon, and its first nucleotide is indexed as the 0th nucleotide, with negative indices in the 5' direction, and positive indices in the 3' direction. Each codon and nucleotide feature is converted to a binary vector via one-hot encoding, and these vectors are concatenated as input into the regression models. The model also accepts RNA folding energies from the RNAfold package, and allows the user to define window sizes and positions to score RNA structure and include as inputs into the regression models. In our best-performing model, codons −5 to +4 and nucleotides −15 to +14 were chosen, as well as folding energies from three 30-nt windows starting at nucleotides −17, −16, and −15.

Model Construction

All models were constructed as feedforward artificial neural networks, using the Python packages Lasagne v. 0.2.dev1[37] and Theano v. 0.9.0[38]. Each network contained one fully connected hidden layer of 200 units with a tanh activation function, and an output layer of one unit with a ReLU activation function. Models were trained using mini-batch stochastic gradient descent with Nesterov momentum (batch size 500).

Comparisons to Other Models

RUST[19] was run via https://ribogalaxy.ucc.ie/ according to the authors' instructions. First, we computed a codon metafootprint on the Weinberg dataset, aligned to the transcriptome as described above. We used an A-site offset of 15 and limited the analysis to 28-nt footprints (the most abundant), in keeping with the authors' analysis. Then, we ran the "similarity of observed and expected profiles" analysis using that codon metafootprint and retrieved the correlation of the observed and expected footprint distribution for each individual gene.

Riboshape[15] was downloaded from https://sourceforge.net/projects/riboshape/ on Feb. 2, 2018. We generated the riboshape data structure according to the README file, with custom scripts (process_data.py and make_data_structure.m, available on GitHub), on our processed footprint counts data from the Weinberg dataset. We restricted the analysis to the 2170 genes present in both our transcriptome and the chxdata.mat data structure that is shipped with riboshape. We binned our genes by truncated lengths 100-210, 211-460, 461-710, 711-960, and 961-4871, which matched the bins in Liu and Song after accounting for our 20 codon truncation regions at either end of genes. Then we trained riboshape models on these bins, using a parameters of 1, 3, 5, 12.5, 25, 37.5, 50, and 75. We report the per gene correlations between the true footprint data and their regression fits (waveforms) in their wavelet decomposition subspace with the least amount of denoising. The values in this subspace are closest to the observed footprint data, and their model trained for this subspace performs the best at predicting observed footprint density. We also report for each subspace the correlation between their denoised footprint data and the regression fits in that subspace. The prior is more directly comparable to our work.

Feature Importance Measurements

A series of leave-one-out models was trained, excluding one codon position at a time from the sequence neighborhood. The importance of each codon position to predictive performance was computed as the difference in MSE between the reduced and full models.

The contribution of codon c at position i to predicted scaled counts was calculated as the average increase in predicted scaled counts due to having that codon at that position, over all instances where codon c was observed at position i in the test set. This increase was computed relative to the expected predicted scaled counts when the codon at position i was varied according to its empirical frequency in the test set (Supplementary Note 2).

Sequence Optimization

The overall translation time of a coding sequence was computed as the sum of the predicted scaled counts over all codons in that coding sequence. This quantity corresponds to total translation time in arbitrary units. A dynamic programming algorithm was developed to find the fastest and slowest translated coding sequences in the set of synonymous coding sequences for a given protein, under a predictive model of scaled counts (Supplementary Note 3). This algorithm runs in $O(CM^L)$ time, where C is the length of the coding sequence in codons, M is the maximum multiplicity of synonymous codons (i.e. 6), and L is the length in codons of the predictive model's sequence neighborhood. This achieves considerable efficiency over the naive $O(C^L)$ model, by assuming that only codons within the sequence neighborhood influence scaled counts.

This algorithm was used to determine the fastest and slowest translating coding sequences for eCitrine, under a predictive model using a sequence window from codons −3 to +2, and using no structure features. Then 100,000 synonymous coding sequences for eCitrine were generated by selecting a synonymous codon uniformly at random for each amino acid. These coding sequences were scored, and the sequences at the 0th, 33rd, 67th, and 100th percentiles were selected for expression experiments.

Measuring Circularization Efficiency

We designed oligonucleotides that mimic the structure of the single-stranded cDNA molecule that is circularized by CircLigase during the M$^c$Glincy & Ingolia (2017) ribosome profiling protocol. These oligonucleotides have the structure:

(SEQ ID NO. 14)
/5Phos/AGATCGGAAGAGCGTCGTGTAGGGAAAGAG/iSp18/GTGACT
GGAGTTCAGACGTGTGCTCTTCCGATCACAGTCATCGTTCGCATTACCCT
GTTATCCCTAAJJJ, where /5Phos/ indicates a 5' phosphorylation; /iSP18/ indicates an 18-atom hexa-ethyleneglycol spacer; and JJJ indicates the reverse complement of the nucleotides at the 5' of the footprint favored or disfavored under the model (oligos defined in Supplementary Table a). Circularization reactions were performed using CircLigase I or II (Epicentre) as described in the manufacturer's instructions, using 1 pmol oligonucleotide in each reaction. Circularization reactions were diluted 1/20 before being subjected to qPCR using DyNAmo HS SYBR Green qPCR Kit (Thermo Scientific) on a CFX96 Touch Real Time PCR Detection System (Biorad). For each circularization reaction, two qPCR reactions were performed: one where the formation of a product was dependent upon oligo circularization, and one where it was not. qPCR data was analyzed using custom R scripts whose core functionality is based on the packages qpcR[39] & dpcR[40] (qpcr_functions.R, available on github). The signal from the circularization dependent amplicon was normalized to that from the circularization independent amplicon, and then expressed as a fold-change compared to the mean of the oligonucleotide with the most favored sequence under the model.

Plasmid and Yeast Strain Construction

Yeast integrating plasmids expressing either mCherry or a differentially optimized version of eCitrine were constructed. The differentially optimized versions of eCitrine were synthesized as gBlocks by Integrated DNA Technologies inserted into the plasmid backbone by Gibson assembly[41]. Transcription of both mCherry and eCitrine is directed by a PGK1 promoter and an ADH1 terminator. To enable yeast transformants to grow in the absence of leucine, the plasmids contain the LEU2 expression cassette from *Kluyveromyces lactis* taken from pUG73[42], which was obtained from EUROSCARF. To enable integration into the yeast genome, the plasmids contain two 300 bp sequences from the his3Δ1 locus of BY4742. To construct yeast strains expressing these plasmids, the plasmids were linearized at the SbfI site and ~1 μg linearized plasmid was used to transform yeast by the high efficiency lithium acetate/single-stranded carrier DNA/PEG method, as described[43]. Transformants were selected by growth on SCD-LEU plates, and plasmid integration into the genome was confirmed by yeast colony PCR with primers flanking both the upstream and downstream junctions between the plasmid sequence and the genome. PCR was performed using GoTaq DNA polymerase (Promega M8295). Haploid BY4742 and BY4741 strains expressing the eCitrine variants and mCherry, respectively, were then mated. For each eCitrine variant, eight transformants were mated to a single mCherry transformant. Diploids were isolated by their ability to grow on SCD-MET-LYS plates. Strains with sequence-confirmed mutations or copy number variation were excluded from further analysis.

Assessing Fluorescent Protein Expression by Flow Cytometry

Overnight cultures of diploid yeast in YEPD were diluted in YEPD so that their optical density at 600 nm ($OD_{600}$) was equal to 0.1 in a 1 mL culture, and then grown for six hours in a 2 mL deep-well plate supplemented with a sterile glass bead, at 30° C. with shaking at 250 rpm. This culture was pelleted by five minutes centrifugation at 3000×g and fixed by resuspension in 16% paraformaldehyde followed by 30 minutes incubation in the dark at room temperature. Cells were washed twice in DPBS (Gibco 14190-44) and stored in DPBS at 4° C. until analysis. Upon analysis, cells were diluted ca. 1:4 in DPBS and subject to flow cytometry measurements on a BD Biosciences (San Jose, Calif.) LSR Fortessa X20 analyzer. Forward Light Scatter measurements (FSC) for relative size, and Side-Scatter measurements (SSC) for intracellular refractive index were made using the 488 nm laser. eCitrine fluorescence was measured using the 488 nm (Blue) laser excitation and detected using a 505 nm Long Pass optical filter, followed by 530/30 nm optical filter with a bandwidth of 30 nm (530/30, or 515 nm-545 nm). mCherry fluorescence was measured using a 561 nm (yellow-green) laser, for excitation and a 595 nm long-pass optical filter, followed by 610/20 nm band-pass optical filter with a bandwidth of 20 nm (or 600 nm-620 nm). PMT values for each color channel were adjusted such that the mean of a sample of BY4743 yeast was 100. 50000 events were collected for each sample. Flow cytometry data was analyzed using a custom R script (gateFlowData.R, available on github) whose core functionality is based on the Bioconductor packages flowCore[44], flowStats, and flowViz[45]. In summary, for each sample, events that had values for red or yellow fluorescence that were less that one had those values set to one. Then, in order to select events that represented normal cells, we used the curv2filter method to extract events that had FSC and side-scatter SSC values within the values of the region of highest local density of all events as considered by their FSC and SSC values. For these events the red fluorescence intensity was considered a measure of mCherry protein expression and yellow fluorescence intensity a measure of eCitrine protein expression.

Measuring eCitrine and mCherry mRNA Expression by qRT-PCR

Overnight cultures of diploid yeast in YEPD were diluted in YEPD so that their $OD_{600}$ was equal to 0.1 in a 20 mL culture, and then grown at 30° C. with shaking at 250 rpm until their $OD_{600}$ reached 0.4-0.6. 10 mL of culture was then pelleted by centrifugation for 5 minutes at 3000×g and snap frozen in liquid nitrogen. Total RNA was extracted from pelleted yeast cultures according to the method of Ares[46]. Thereafter, 10 Cpg of this RNA was treated with Turbo DNase I (ambion) according to the manufacturer's instructions, then 1 μg DNase treated RNA was reverse transcribed using anchored oligo dT and Protoscript II (NEB) according to the manufacturer's instructions. ½0$^{th}$ of this reaction was then subjected to qPCR using the DyNAmo HS SYBR Green qPCR Kit (Thermo Scientific) on a CFX96 Touch Real Time PCR Detection System (Biorad). For each reverse transcription reaction, two qPCR reactions were performed: one with primers specific to the mCherry ORF, and one with primers specific to the eCitrine variant ORF in question. qPCR data was analyzed using custom R scripts whose core functionality is based on the packages qpcR[39,46] & dpcR[40] (qpcr_functions.R, available on github). The signal from each eCitrine variant ORF was normalized to that from the mCherry ORF in the same sample, and then expressed as a fold-change compared to the median of these values for the MIN (fastest predicted sequence) eCitrine variant.

Supplementary Note 1: Biological Signal and Bias

Experimental counts of ribosome footprints reflect a mix of biological signal and technical biases. Our model with a window of 30 nucleotides (codons −5 to +4) successfully captures this same mix of signal and bias, without distinguishing the two. Predictions from that model are simply predicting the data one would get from a ribosome profiling experiment.

But recapitulating biased data is not the ultimate goal; we would prefer to capture unbiased biological infor-mation. We hypothesized that the anomalously high influences of the ends of the 30 nt region represented enzyme biases. Our model can quantify the contribution of specific end sequences to higher or lower footprint count (again, without a priori calling it signal or noise). We tested the enzyme activity on different substrates and showed that our quantitative predictions for those end sequences correlate very well with actual enzyme preferences. That meant that much of the influence of the end sequences is on footprint recovery, not true ribosome distribution.

Going forward from there, to test the biological predictions of our model, we excluded those end regions because their contribution was mostly an artifact. A model based on codons −3 to +2 will not recapitulate the experimental data as well, because those data are influenced by technical artifacts. But, we hypothesized that this reduced −3:2 model would still capture biological information. We used this reduced model to design sequences we expected to be translated at different speeds, and we saw a surprisingly good correlation between the fluorescent protein output and the models prediction. From this, we concluded that our model had learned substantial biological information in codons −3 to +2, that this information was enough to predict true ribosome distribution quite well, and that we had avoided substantial bias in the ends of the footprints during model training by removing them from our input features, enough to make good biological predictions.

Supplementary Note 2: Feature Importance Codon Scores $s_{x,i}$=codon score for codon x in position i average increase in predicted scaled counts when codon x is observed in position i $T_{te}$=number of transcripts in test set $C_t$=length of CDS t in codons t=index over transcripts c=index over codons $\kappa(t, C)$=function that returns the codon at position (t, c)

$v(t, c)$=function that returns the sequence neighborhood around position (t, c)

$v_{d,i}(t, c)$=function that returns the sequence neighborhood around position (t, c), replaces the codon at position i with codon d $$p_i(d) = \frac{\sum_{t=1}^{T_{te}}\sum_{c=1}^{C_t} 1(\kappa(t, c+i) = d)}{\sum_{s=1}^{T_{te}} C_s}$$

$f$=prediction function of the neural network model $$s_{x,i} = \frac{1}{\sum_{t=1}^{T_{te}}\sum_{c=1}^{C_t} 1(\kappa(t, c+i) = x)}$$

-continued $$\sum_{t=1}^{T_{te}}\sum_{c=1}^{C_t} 1(\kappa(t, c+i) = x)\left[f(v(t, c)) - \sum_{d \in \{ACGT\}^3} p_i(d) f(v_{d,i}(t, c))\right]$$

Supplementary Note 3: Translation Rate Optimization Algorithm

L=length of coding sequence in codons

A=amino acid sequence of protein

A[m: n]=slice of A from positions m to n, 1 indexed. Negative indices count from end.

i=index over A site codons in coding sequence $c_{rel}^{min}$=min. index of a codon in the sequence neighborhood, relative to A site (e.g., −7)

$c_{rel}^{max}$=max. index of a codon in the sequence neighborhood, relative to A site (e.g., 5)

$\phi(a)$=function that returns the set of synonymous codons for amino acid a $\xi([a_1, a_2, \ldots, a_n]) = \phi(a_1) \times \phi(a_2) \times \ldots \times \phi(a_n)$ $f$=prediction function of the neural network model Algorithm 1 Calculate fastest codon sequence under a predictive model†

```
for i ∈ {1 ... L} do
    c_i^min = max(1, i + c_rel^min)    ▷1
    c_i^max = min(i + c_rel^max, L)    ▷2
    Q_i = ξ(A[c_i^min : c_i^max])      ▷3
    for q ∈ Q_i do
        T_{i,q} ← f(q)††
    end for
end for
for i ∈ {1 ... L} do
    if c_min^i == 1 then
        for q ∈ Q_i do
            P_{i,q} ← None
            V_{i,q} ← T_{i,q}
        end for
    else if c_min^i > 1 then
        for q ∈ Q_i do
            P_{i,q} ←   argmin   V[i − 1](p)
                     p∈φ(A[c_min^i −1])×q[:−3]
            V_{i,q} ← V_{i−1,P_{i,q}} + T_{i,q}
        end for
    end if
end for
q_L = argmin V_{L,q}
       q∈Q_L
i = L; q_i = q_L; cds = q_L
while c_min^i > 1 do
    i −= 1
    q_i ← P_{i,q}
    cds ← q_i[: 3] + cds
end while
return cds
```

▷1 Minimum codon idx in neighborhood around position i
▷2 Maximum codon idx in neighborhood around position i
▷3 Set of sequence neighborhoods
†To calculate slowest sequence, change argmins to argmax
††If the sequence neighborhood is truncated because it runs outside of the coding sequence, we input this part of the neighborhood to our model as all 0 values (i.e. no codons are encoded as 1), Average per gene correlations between ribosome footprint counts (Weinberg et al. 2016) and predictions of these counts. Liu V0-V7, performance of Riboshape (Liu and Song, 2016), shown as average correlations per gene between denoised ribosome footprint data and predictions of that denoised data. Riboshape projects data into 8 subspaces of a Debauchies-8 basis for wavelet analysis. $V_0$ is the lowest resolution projection (most smoothed), and $V_7$ is the closest approximation of the raw data. Tunney, performance of Iχnos, shown as the average correlation per gene between true ribosome footprint data and predictions of that data. All results are reported on 1711 yeast genes, taking an intersection between genes used in the 'chxdata.mat' file published with riboshape, genes that passed filtering in our RUST analysis, and genes in our yeast transcriptome, excluding the I$\chi$nos training set.

SUPPLEMENTARY TABLE 1

Performance comparison with riboshape

| Liu $V_0$ | Liu $V_1$ | Liu $V_2$ | Liu $V_3$ | Liu $V_4$ | Liu $V_5$ | Liu $V_6$ | Liu $V_7$ | Tunney |
|---|---|---|---|---|---|---|---|---|
| 0.39 | 0.48 | 0.51 | 0.50 | 0.50 | 0.50 | 0.50 | 0.47 | 0.56 |

Average per gene correlations between ribosome footprint counts (Weinberg et al. 2016) and predictions of these counts. Liu V0-V7, performance of Riboshape (Liu and Song, 2016), shown as average correlations per gene between denoised ribosome footprint data and predictions of that denoised data. Riboshape projects data into 8 subspaces of a Debauchies-8 basis for wavelet analysis. $V_0$ is the lowest resolution projection (most smoothed), and $V_7$ is the closest approximation of the raw data. Tunney, performance of I$\chi$nos, shown as the average correlation per gene between true ribosome footprint data and predictions of that data. All results are reported on 1711 yeast genes, taking an intersection between genes used in the 'chxdata.mat' file published with riboshape, genes that passed filtering in our RUST analysis, and genes in our yeast transcriptome, excluding the I$\chi$nos training set.

SUPPLEMENTARY TABLE 2

Oligos used in strain construction and measuring mRNA abundance and ligation efficiency Genotyping; upstream flank,
F primer; product 534 bp:
(SEQ ID NO. 15)
TGCATAAACGCTGTTGGTGC Genotyping; upstream flank,
R primer; product 534 bp:
(SEQ ID NO. 16)
AGAGTCATCCGCTAGGTGGA Genotyping; downstream flank,
F primer; product 552 bp:
(SEQ ID NO. 17)
AGGTGGCAAGTGGTATTCCG Genotyping; downstream flank,
R primer; product 552 bp:
(SEQ ID NO. 18)
ACAGGTGTTGGCTTGGTGAA Circularization dependent qPCR;
F primer; product 100 bp:
(SEQ ID NO. 19)
CTCTTTCCCTACACGACGCTC Circularization dependent qPCR;
R primer; product 100 bp:
(SEQ ID NO. 20)
GTGACTGGAGTTCAGACGTGTG Circularization independent qPCR;
F primer; product 62 bp:
(SEQ ID NO. 21)
GTGACTGGAGTTCAGACGTGTG SUPPLEMENTARY TABLE 2-continued Oligos used in strain construction and measuring mRNA abundance and ligation efficiency Circularization independent qPCR;
R primer; product 62 bp:
(SEQ ID NO. 22)
GATAACAGGGTAATGCGAACGA Model seq: ATA:
(SEQ ID NO. 23)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAATAT Model seq: TCC:
(SEQ ID NO. 24)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAAGGA Model seq: CCA:
(SEQ ID NO. 25)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAATGG Model seq: CAC:
(SEQ ID NO. 26)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAAGTG Model seq: AGG:
(SEQ ID NO. 27)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAACCT Model seq: TTG:
(SEQ ID NO. 28)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAACAA Model seq: CGT:
(SEQ ID NO. 29)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAAACG Model seq: GAC:
(SEQ ID NO. 30)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAAGTC Model seq: GGG:
(SEQ ID NO. 31)
/5P/AGATCGGAAGAGCGTCGTGTAGGGAAAGAG/iSp18/GTGACTGGA
GTTCAGACGTGTGCTCTTCCGATCACAGTCATCGTTCGCATTACCCTGTT
ATCCCTAACCC mCherry qPCR F:
(SEQ ID NO. 32)
CATGGTCTTCTTCTGCATTACG mCherry qPCR R:
(SEQ ID NO. 33)
GACTACTTGAAGCTGTCCTTC eCitrine UTR R:
(SEQ ID NO. 34)
CGCTTATTTAGAAGTGGCG eCitrine MIN F:
(SEQ ID NO. 35)
GCCCTCTCCAAAGATCC SUPPLEMENTARY TABLE 2-continued Oligos used in strain construction and
measuring mRNA abundance and ligation efficiency eCitrine 000 F:
(SEQ ID NO. 36)
GCTCTATCTAAAGACCCAAACG eCitrine 333 F:
(SEQ ID NO. 37)
GCATTATCGAAGGACCCTAA eCitrine 666 F:
(SEQ ID NO. 38)
GCTCTATCTAAGGACCCCAA eCitrine 999 F:
(SEQ ID NO. 39)
GCGTTAAGCAAAGACCC eCitrine MAX F:
(SEQ ID NO. 40)
GCACTGAGCAAGGACCC eCitrine PAR F:
(SEQ ID NO. 41)
GCCTTATCCAAAGATCCAAA

REFERENCES

1. Ishimura, R. et al. Ribosome stalling induced by mutation of a CNS-specific tRNA causes neurodegeneration. *Science* 345, 455-459 (2014).
2. Goodarzi, H. et al. Modulated Expression of Specific tRNAs Drives Gene Expression and Cancer Progression. *Cell* 165, 1416-1427 (2016).
3. Kirchner, S. et al. Alteration of protein function by a silent polymorphism linked to tRNA abundance. *PLoS Biol.* 15, e2000779 (2017).
4. Zhao, F., Yu, C.-H. & Liu, Y. Codon usage regulates protein structure and function by affecting translation elongation speed in *Drosophila* cells. *Nucleic Acids Res.* 45, 8484-8492 (2017).
5. Shah, P., Ding, Y., Niemczyk, M., Kudla, G. & Plotkin, J. B. Rate-limiting steps in yeast protein translation. *Cell* 153, 1589-1601 (2013).
6. Presnyak, V. et al. Codon optimality is a major determinant of mRNA stability. *Cell* 160, 1111-1124 (2015).
7. Bazzini, A. A. et al. Codon identity regulates mRNA stability and translation efficiency during the maternal-to-zygotic transition. *EMBO J.* 35, 2087-2103 (2016).
8. Ingolia, N. T., Ghaemmaghami, S., Newman, J. R. S. & Weissman, J. S. Genome-wide analysis in vivo of translation with nucleotide resolution using ribosome profiling. *Science* 324, 218-223 (2009).
9. Stadler, M. & Fire, A. Wobble base-pairing slows in vivo translation elongation in metazoans. *RNA* 17, 2063-2073 (2011).
10. Dana, A. & Tuller, T. Determinants of translation elongation speed and ribosomal profiling biases in mouse embryonic stem cells. *PLoS Comput. Biol.* 8, e1002755 (2012).
11. Charneski, C. A. & Hurst, L. D. Positively charged residues are the major determinants of ribosomal velocity. *PLoS Biol.* 11, e1001508 (2013).
12. Gardin, J. et al. Measurement of average decoding rates of the 61 sense codons in vivo. *Elife* 3, e03735 (2014).
13. Lareau, L. F., Hite, D. H., Hogan, G. J. & Brown, P. O. Distinct stages of the translation elongation cycle revealed by sequencing ribosome-protected mRNA fragments. *Elife* 3, e01257 (2014).
14. Pop, C. et al. Causal signals between codon bias, mRNA structure, and the efficiency of translation and elongation. *Mol. Syst. Biol.* 10, 770 (2014).
15. Liu, T.-Y. & Song, Y. S. Prediction of ribosome footprint profile shapes from transcript sequences. *Bioinformatics* 32, i183-i191 (2016).
16. Zhang, S. et al. Analysis of Ribosome Stalling and Translation Elongation Dynamics by Deep Learning. *Cell Syst* 5, 212-220.e6 (2017).
17. Dao Duc, K. & Song, Y. S. The impact of ribosomal interference, codon usage, and exit tunnel interactions on translation elongation rate variation. *PLoS Genet.* 14, e1007166 (2018).
18. Fang, H. et al. Scikit-ribo Enables Accurate Estimation and Robust Modeling of Translation Dynamics at Codon Resolution. *Cell Syst* 6, 180-191.e4 (2018).
19. O'Connor, P. B. F., Andreev, D. E. & Baranov, P. V. Comparative survey of the relative impact of mRNA features on local ribosome profiling read density. *Nat. Commun.* 7, 12915 (2016).
20. Artieri, C. G. & Fraser, H. B. Accounting for biases in riboprofiling data indicates a major role for proline in stalling translation. *Genome Res.* 24, 2011-2021 (2014).
21. Hussmann, J. A., Patchett, S., Johnson, A., Sawyer, S. & Press, W. H. Understanding Biases in Ribosome Profiling Experiments Reveals Signatures of Translation Dynamics in Yeast. *PLoS Genet.* 11, e1005732 (2015).
22. Weinberg, D. E. et al. Improved Ribosome-Footprint and mRNA Measurements Provide Insights into Dynamics and Regulation of Yeast Translation. *Cell Rep.* 14, 1787-1799 (2016).
23. Sharp, P. M., Tuohy, T. M. & Mosurski, K. R. Codon usage in yeast: cluster analysis clearly differentiates highly and lowly expressed genes. *Nucleic Acids Res.* 14, 5125-5143 (1986).
24. Plotkin, J. B. & Kudla, G. Synonymous but not the same: the causes and consequences of codon bias. *Nat. Rev. Genet.* 12, 32-42 (2011).
25. dos Reis, M., Savva, R. & Wernisch, L. Solving the riddle of codon usage preferences: a test for translational selection. *Nucleic Acids Res.* 32, 5036-5044 (2004).
26. Letzring, D. P., Dean, K. M. & Grayhack, E. J. Control of translation efficiency in yeast by codon-anticodon interactions. *RNA* 16, 2516-2528 (2010).
27. Gamble, C. E., Brule, C. E., Dean, K. M., Fields, S. & Grayhack, E. J. Adjacent Codons Act in Concert to Modulate Translation Efficiency in Yeast. *Cell* 166, 679-690 (2016).
28. Murphy, F. V., 4th & Ramakrishnan, V. Structure of a purine-purine wobble base pair in the decoding center of the ribosome. *Nat. Struct. Mol. Biol.* 11, 1251-1252 (2004).
29. McGlincy, N. J. & Ingolia, N. T. Transcriptome-wide measurement of translation by ribosome profiling. *Methods* 126, 112-129 (2017).
30. Iwasaki, S., Floor, S. N. & Ingolia, N. T. Rocaglates convert DEAD-box protein eIF4A into a sequence-selective translational repressor. *Nature* 534, 558-561 (2016).
31. Schuller, A. P., Wu, C. C.-C., Dever, T. E., Buskirk, A. R. & Green, R. eIF5A Functions Globally in Translation Elongation and Termination. *Mol. Cell* 66, 194-205.e5 (2017).
32. Sheff, M. A. & Thorn, K. S. Optimized cassettes for fluorescent protein tagging in *Saccharomyces cerevisiae*. *Yeast* 21, 661-670 (2004).

33. Chu, D. et al. Translation elongation can control translation initiation on eukaryotic mRNAs. *EMBO J.* 33, 21-34 (2013).
34. Qian, W., Yang, J.-R., Pearson, N. M., Maclean, C. & Zhang, J. Balanced Codon Usage Optimizes Eukaryotic Translational Efficiency. *PLoS Genet.* 8, e1002603 (2012).

METHODS-ONLY REFERENCES

35. Langmead, B., Trapnell, C., Pop, M. & Salzberg, S. L. Ultrafast and memory-efficient alignment of short DNA sequences to the human genome. *Genome Biol.* 10, R25 (2009).
36. Li, B. & Dewey, C. N. RSEM: accurate transcript quantification from RNA-Seq data with or without a reference genome. *BMC Bioinformatics* 12, 323 (2011).
37. Battenberg, E. et al. *Lasagne: First release*. (2015). doi:10.5281/zenodo.27878
38. The Theano Development Team et al. Theano: A Python framework for fast computation of mathematical expressions. *arXiv* (2016).
39. Ritz, C. & Spiess, A.-N. qpcR: an R package for sigmoidal model selection in quantitative real-time polymerase chain reaction analysis. *Bioinformatics* 24, 1549-1551 (2008).
40. Burdukiewicz, M. et al. Methods for comparing multiple digital PCR experiments. *Biomol Detect Quantif* 9, 14-19 (2016).
41. Gibson, D. G. et al. Enzymatic assembly of DNA molecules up to several hundred kilobases. *Nat. Methods* 6, 343-345 (2009).
42. Gueldener, U., Heinisch, J., Koehler, G. J., Voss, D. & Hegemann, J. H. A second set of loxP marker cassettes for Cre-mediated multiple gene knockouts in budding yeast. *Nucleic Acids Res.* 30, e23 (2002).
43. Daniel Gietz, R. & Woods, R. A. Transformation of yeast by lithium acetate/single-stranded carrier DNA/polyethylene glycol method. in *Methods in Enzymology* 87-96 (2002).
44. Hahne, F. et al. flowCore: a Bioconductor package for high throughput flow cytometry. *BMC Bioinformatics* 10, 106 (2009).
45. Sarkar, D., Le Meur, N. & Gentleman, Using flowViz to visualize flow cytometry data. *Bioinformatics* 24, 878-879 (2008).
46. Ares, M. Isolation of total RNA from yeast cell cultures. *Cold Spring Harb. Protoc.* 2012, 1082-1086 (2012).

The invention claimed is:

1. A method for tailoring gene transcript sequences for protein expression, comprising steps:
   a) measuring ribosome dynamics in an organism or cell type of interest to obtain ribosome profiling data;
   b) training a statistical model of the relationship between DNA sequence and translation speed on the ribosome profiling data; and
   c) using the trained model to design a DNA sequence encoding and tailored for expression of a protein of interest,
   wherein step (b) comprises training the model to learn sequence preferences for translation by using counts of fragments at each codon position to learn the cell type or organism's sequence preferences for fast translation, by:
   counting how many ribosomes are seen at each codon position in each gene transcript, normalized by the average number of ribosomes per position in that gene transcript;
   using a machine learning protocol to learn the model for the position-to-normalized count relationship of the genome, wherein a 30-40 nucleotide window is encoded around each codon feature; and
   training a neural network to predict normalized counts as a function of these features, providing the model that can take as input any arbitrary gene transcript sequence and predict how ribosomes will slow down or speed up on that sequence.

2. The method of claim 1 wherein step (b) comprises:
   predicting counts at the A site codon, wherein a sequence neighborhood spanning from 5 codons upstream of the A site (codon −5) to 4 codons downstream of the A site (codon+4) is used as the predictive region;
   dividing the neighborhood into codons, wherein each codon and nucleotide is converted to a binary vector via one-hot encoding for input into regression models;
   computing RNA structure score on three 30 nt sliding structure windows that span the width of a typical 28 nt footprint, wherein the windows start 17, 16, and 15 nucleotides before the start of the A site; and
   concatenating the vector as the input to a fully connected feed-forward neural network model.

3. The method of claim 1 wherein step (c) comprises using the model to design an optimized codon sequence to encode a given protein sequence by using a dynamic programming algorithm to determine an optimal codon sequence in the set of synonymous sequences that code for the protein.

4. The method of claim 2 wherein the model also accepts RNA folding energies and allows a user to define window sizes and positions to score RNA structure and include as inputs into the regression models.

5. The method of claim 2 wherein the model includes codons −5 to +4 and nucleotides −15 to +14, as well as folding energies from three 30-nt windows starting at nucleotides −17, −16, and −15.

6. The method of claim 1 further comprising synthesizing a DNA molecule of the DNA sequence.

7. The method of claim 2 further comprising synthesizing a DNA molecule of the DNA sequence.

8. The method of claim 3 further comprising synthesizing a DNA molecule of the DNA sequence.

9. The method of claim 4 further comprising synthesizing a DNA molecule of the DNA sequence.

10. The method of claim 5 further comprising synthesizing a DNA molecule of the DNA sequence.

* * * * *

SEQUENCE LISTING

```
<160> NUMBER OF SEQ ID NOS: 41

<210> SEQ ID NO 1
<211> LENGTH: 42
<212> TYPE: DNA
<213> ORGANISM: Artificial Sequence
<220> FEATURE:
<223> OTHER INFORMATION: DEPICTED SEQUENCE OF NEURAL NETWORK STRUCTURE

<400> SEQUENCE: 1
agcatttctt gccaagaaag agagctgcct ccatcagagc ct                          42

<210> SEQ ID NO 2
<211> LENGTH: 36
<212> TYPE: DNA
<213> ORGANISM: Artificial Sequence
<220> FEATURE:
<223> OTHER INFORMATION: DEPICTED SEQUENCE OF NEURAL NETWORK MODEL

<400> SEQUENCE: 2
gctaacttga tggccggtca ctgggttgct atctcc                                 36

<210> SEQ ID NO 3
<211> LENGTH: 36
<212> TYPE: DNA
<213> ORGANISM: Artificial Sequence
<220> FEATURE:
<223> OTHER INFORMATION: DEPICTED SEQUENCE OF NEURAL NETWORK STRUCTURE

<400> SEQUENCE: 3
cacttgaaga gaaactttac gaataacact acggaa                                 36

<210> SEQ ID NO 4
<211> LENGTH: 61
<212> TYPE: DNA
<213> ORGANISM: Artificial Sequence
<220> FEATURE:
<223> OTHER INFORMATION: DEPICTED SEQUENCE OF NEURAL NETWORK STRUCTURE

<400> SEQUENCE: 4
```

```
tgcatgctgc atctgcatgc atgcatgcat gcatgcatgc atgcatgcat gcatgcatgc    60
a                                                                    61

<210> SEQ ID NO 5
<211> LENGTH: 15
<212> TYPE: PRT
<213> ORGANISM: Aequorea victoria

<400> SEQUENCE: 5

Ala Thr Gly Ala Gly Thr Ala Ala Ala Gly Gly Ala Gly Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: AMINO ACID SEQUENCE

<400> SEQUENCE: 6

Ala Thr Gly Thr Cys Cys Ala Ala Ala Gly Gly Thr Gly Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: AMINO ACID SEQUENCE

<400> SEQUENCE: 7

Ala Thr Gly Thr Cys Ala Ala Ala Ala Gly Gly Cys Gly Ala Gly
1               5                   10                  15

<210> SEQ ID NO 8
<211> LENGTH: 37
<212> TYPE: DNA
<213> ORGANISM: Artificial Sequence
<220> FEATURE:
<223> OTHER INFORMATION: n is random nucleotides
<220> FEATURE:
<221> NAME/KEY: misc_feature
<222> LOCATION: (1)..(5)
<223> OTHER INFORMATION: n is a, c, g, or t

<400> SEQUENCE: 8
nnnnnagcta agatcggaag agcacacgtc tgaaddc                             37

<210> SEQ ID NO 9
<211> LENGTH: 55
<212> TYPE: DNA
<213> ORGANISM: Artificial Sequence
<220> FEATURE:
<223> OTHER INFORMATION: MODIFIED RT PRIMER

<400> SEQUENCE: 9
agatcggaag agcgtcgtgt agggaaagag gtgactggag ttcagacgtg tgctc         55

<210> SEQ ID NO 10
<211> LENGTH: 21
<212> TYPE: DNA
<213> ORGANISM: Artificial Sequence
<220> FEATURE:
<223> OTHER INFORMATION: LINKER SEQUENCE

<400> SEQUENCE: 10
```
tcgtatgccg tcttctgctt g                                              21

<210> SEQ ID NO 11
<211> LENGTH: 30
<212> TYPE: DNA
<213> ORGANISM: Artificial Sequence
<220> FEATURE:
<223> OTHER INFORMATION: LINKER SEQUENCE
<220> FEATURE:
<221> NAME/KEY: misc_feature
<222> LOCATION: (1)..(5)
<223> OTHER INFORMATION: n is a, c, g, or t

<400> SEQUENCE: 11
nnnnnagatc ggaagagcac acgtctgaac                                     30

<210> SEQ ID NO 12
<211> LENGTH: 17
<212> TYPE: DNA
<213> ORGANISM: Artificial Sequence
<220> FEATURE:
<223> OTHER INFORMATION: LINKER SEQUENCE

<400> SEQUENCE: 12
ctgtaggcac catcaat                                                   17

<210> SEQ ID NO 13
<211> LENGTH: 17
<212> TYPE: DNA
<213> ORGANISM: Artificial Sequence
<220> FEATURE:
<223> OTHER INFORMATION: LINKER SEQUENCE

<400> SEQUENCE: 13
ctgtaggcac catcaat                                                   17

<210> SEQ ID NO 14
<211> LENGTH: 98
<212> TYPE: DNA
<213> ORGANISM: Artificial Sequence
<220> FEATURE:
<223> OTHER INFORMATION: OLIGONUCLEOTIDE STRUCTURE

<400> SEQUENCE: 14
agatcggaag agcgtcgtgt agggaaagag sgtgactgga gttcagacgt gtgctcttcc    60
gatcacagtc atcgttcgca ttaccctgtt atccctaa                            98

<210> SEQ ID NO 15
<211> LENGTH: 20
<212> TYPE: DNA
<213> ORGANISM: Artificial Sequence
<220> FEATURE:
<223> OTHER INFORMATION: UPSTREAM FLANK,F PRIMER

<400> SEQUENCE: 15
tgcataaacg ctgttggtgc                                                20

<210> SEQ ID NO 16
<211> LENGTH: 20
<212> TYPE: DNA
<213> ORGANISM: Artificial Sequence
<220> FEATURE:
<223> OTHER INFORMATION: UPSTREAM FLANK,R PRIMER

<400> SEQUENCE: 16

| | |
|---|---|
| agagtcatcc gctaggtgga | 20 |

<210> SEQ ID NO 17
<211> LENGTH: 20
<212> TYPE: DNA
<213> ORGANISM: Artificial Sequence
<220> FEATURE:
<223> OTHER INFORMATION: DOWNSTREAM FLANK,F PRIMER

<400> SEQUENCE: 17

| | |
|---|---|
| aggtggcaag tggtattccg | 20 |

<210> SEQ ID NO 18
<211> LENGTH: 20
<212> TYPE: DNA
<213> ORGANISM: Artificial Sequence
<220> FEATURE:
<223> OTHER INFORMATION: DOWNSTREAM FLANK, R PRIMER

<400> SEQUENCE: 18

| | |
|---|---|
| acaggtgttg gcttggtgaa | 20 |

<210> SEQ ID NO 19
<211> LENGTH: 21
<212> TYPE: DNA
<213> ORGANISM: Artificial Sequence
<220> FEATURE:
<223> OTHER INFORMATION: CIRCULARIZATION DEPENDENT qPCR,R PRIMER

<400> SEQUENCE: 19

| | |
|---|---|
| ctctttccct acacgacgct c | 21 |

<210> SEQ ID NO 20
<211> LENGTH: 22
<212> TYPE: DNA
<213> ORGANISM: Artificial Sequence
<220> FEATURE:
<223> OTHER INFORMATION: CIRCULARIZATION DEPENDENT qPCR,R PRIMER

<400> SEQUENCE: 20

| | |
|---|---|
| gtgactggag ttcagacgtg tg | 22 |

<210> SEQ ID NO 21
<211> LENGTH: 22
<212> TYPE: DNA
<213> ORGANISM: Artificial Sequence
<220> FEATURE:
<223> OTHER INFORMATION: CIRCULARIZATION INDEPENDENT qPCR,F PRIMER

<400> SEQUENCE: 21

| | |
|---|---|
| gtgactggag ttcagacgtg tg | 22 |

<210> SEQ ID NO 22
<211> LENGTH: 22
<212> TYPE: DNA
<213> ORGANISM: Artificial Sequence
<220> FEATURE:
<223> OTHER INFORMATION: CIRCULARIZATION INDEPENDENT qPCR,R PRIMER

<400> SEQUENCE: 22

| | |
|---|---|
| gataacaggg taatgcgaac ga | 22 |

<210> SEQ ID NO 23
<211> LENGTH: 101
<212> TYPE: DNA
<213> ORGANISM: Artificial Sequence

```
<220> FEATURE:
<223> OTHER INFORMATION: MODEL SEQUENCE ATA

<400> SEQUENCE: 23
agatcggaag agcgtcgtgt agggaaagag sgtgactgga gttcagacgt gtgctcttcc      60
gatcacagtc atcgttcgca ttaccctgtt atccctaata t                         101

<210> SEQ ID NO 24
<211> LENGTH: 100
<212> TYPE: DNA
<213> ORGANISM: Artificial Sequence
<220> FEATURE:
<223> OTHER INFORMATION: MODEL SEQUENCE TCC

<400> SEQUENCE: 24
agatcggaag agcgtcgtgt agggaaagag gtgactggag ttcagacgtg tgctcttccg      60
atcacagtca tcgttcgcat taccctgtta tccctaagga                           100

<210> SEQ ID NO 25
<211> LENGTH: 100
<212> TYPE: DNA
<213> ORGANISM: Artificial Sequence
<220> FEATURE:
<223> OTHER INFORMATION: MODEL SEQUENCE CCA

<400> SEQUENCE: 25
agatcggaag agcgtcgtgt agggaaagag gtgactggag ttcagacgtg tgctcttccg      60
atcacagtca tcgttcgcat taccctgtta tccctaatgg                           100

<210> SEQ ID NO 26
<211> LENGTH: 100
<212> TYPE: DNA
<213> ORGANISM: Artificial Sequence
<220> FEATURE:
<223> OTHER INFORMATION: MODEL SEQUENCE CAC

<400> SEQUENCE: 26
agatcggaag agcgtcgtgt agggaaagag gtgactggag ttcagacgtg tgctcttccg      60
atcacagtca tcgttcgcat taccctgtta tccctaagtg                           100

<210> SEQ ID NO 27
<211> LENGTH: 101
<212> TYPE: DNA
<213> ORGANISM: Artificial Sequence
<220> FEATURE:
<223> OTHER INFORMATION: MODEL SEQUENCE AGG

<400> SEQUENCE: 27
agatcggaag agcgtcgtgt agggaaagag sgtgactgga gttcagacgt gtgctcttcc      60
gatcacagtc atcgttcgca ttaccctgtt atccctaacc t                         101

<210> SEQ ID NO 28
<211> LENGTH: 100
<212> TYPE: DNA
<213> ORGANISM: Artificial Sequence
<220> FEATURE:
<223> OTHER INFORMATION: MODEL SEQUENCE TTG

<400> SEQUENCE: 28
agatcggaag agcgtcgtgt agggaaagag gtgactggag ttcagacgtg tgctcttccg      60
atcacagtca tcgttcgcat taccctgtta tccctaacaa                           100
```

<210> SEQ ID NO 29
<211> LENGTH: 101
<212> TYPE: DNA
<213> ORGANISM: Artificial Sequence
<220> FEATURE:
<223> OTHER INFORMATION: MODEL SEQUENCE CGT

<400> SEQUENCE: 29
agatcggaag agcgtcgtgt agggaaagag sgtgactgga gttcagacgt gtgctcttcc      60
gatcacagtc atcgttcgca ttaccctgtt atccctaaac g                        101

<210> SEQ ID NO 30
<211> LENGTH: 100
<212> TYPE: DNA
<213> ORGANISM: Artificial Sequence
<220> FEATURE:
<223> OTHER INFORMATION: MODEL SEQUENCE GAC

<400> SEQUENCE: 30
agatcggaag agcgtcgtgt agggaaagag gtgactggag ttcagacgtg tgctcttccg      60
atcacagtca tcgttcgcat taccctgtta tccctaagtc                          100

<210> SEQ ID NO 31
<211> LENGTH: 100
<212> TYPE: DNA
<213> ORGANISM: Artificial Sequence
<220> FEATURE:
<223> OTHER INFORMATION: MODEL SEQUENCE GGG

<400> SEQUENCE: 31
agatcggaag agcgtcgtgt agggaaagag gtgactggag ttcagacgtg tgctcttccg      60
atcacagtca tcgttcgcat taccctgtta tccctaacccc                         100

<210> SEQ ID NO 32
<211> LENGTH: 22
<212> TYPE: DNA
<213> ORGANISM: Artificial Sequence
<220> FEATURE:
<223> OTHER INFORMATION: MCHERRY qPCR F

<400> SEQUENCE: 32
catggtcttc ttctgcatta cg                                              22

<210> SEQ ID NO 33
<211> LENGTH: 21
<212> TYPE: DNA
<213> ORGANISM: Artificial Sequence
<220> FEATURE:
<223> OTHER INFORMATION: MCHERRY qPCR R

<400> SEQUENCE: 33
gactacttga agctgtcctt c                                               21

<210> SEQ ID NO 34
<211> LENGTH: 19
<212> TYPE: DNA
<213> ORGANISM: Artificial Sequence
<220> FEATURE:
<223> OTHER INFORMATION: eCitrine UTR R

<400> SEQUENCE: 34
cgcttattta gaagtggcg                                                  19

```
<210> SEQ ID NO 35
<211> LENGTH: 17
<212> TYPE: DNA
<213> ORGANISM: Artificial Sequence
<220> FEATURE:
<223> OTHER INFORMATION: eCitrine MIN F

<400> SEQUENCE: 35
gccctctcca aagatcc                                                    17

<210> SEQ ID NO 36
<211> LENGTH: 22
<212> TYPE: DNA
<213> ORGANISM: Artificial Sequence
<220> FEATURE:
<223> OTHER INFORMATION: eCitrine 000 F

<400> SEQUENCE: 36
gctctatcta aagacccaaa cg                                              22

<210> SEQ ID NO 37
<211> LENGTH: 20
<212> TYPE: DNA
<213> ORGANISM: Artificial Sequence
<220> FEATURE:
<223> OTHER INFORMATION: eCitrine 333 F

<400> SEQUENCE: 37
gcattatcga aggaccctaa                                                 20

<210> SEQ ID NO 38
<211> LENGTH: 20
<212> TYPE: DNA
<213> ORGANISM: Artificial Sequence
<220> FEATURE:
<223> OTHER INFORMATION: eCitrine 666 F

<400> SEQUENCE: 38
gctctatcta aggaccccaa                                                 20

<210> SEQ ID NO 39
<211> LENGTH: 17
<212> TYPE: DNA
<213> ORGANISM: Artificial Sequence
<220> FEATURE:
<223> OTHER INFORMATION: eCitrine 999 F

<400> SEQUENCE: 39
gcgttaagca aagaccc                                                    17

<210> SEQ ID NO 40
<211> LENGTH: 17
<212> TYPE: DNA
<213> ORGANISM: Artificial Sequence
<220> FEATURE:
<223> OTHER INFORMATION: eCitrine MAX F

<400> SEQUENCE: 40
gcactgagca aggaccc                                                    17

<210> SEQ ID NO 41
<211> LENGTH: 20
<212> TYPE: DNA
<213> ORGANISM: Artificial Sequence
<220> FEATURE:
<223> OTHER INFORMATION: eCitrine PAR F
```

```
<400> SEQUENCE: 41
gccttatcca aagatccaaa                                              20
```